United States Patent [19]

Maeda et al.

[11] Patent Number: 5,245,078
[45] Date of Patent: Sep. 14, 1993

[54] PROCESS FOR SEPARATING AN ORGANIC ACID OR ACIDS FROM AN ORGANIC ACID-CONTAINING SOLUTION

[75] Inventors: Toshihiro Maeda; Isao Nakazawa, both of Zama, Japan

[73] Assignee: Mitsubishi Kasei Corporation, Tokyo, Japan

[21] Appl. No.: 786,883

[22] Filed: Nov. 1, 1991

[30] Foreign Application Priority Data

Nov. 2, 1990 [JP] Japan .................................. 2-295427
Nov. 9, 1990 [JP] Japan .................................. 2-304535

[51] Int. Cl.$^5$ .................................................. C07C 51/42
[52] U.S. Cl. .................................... 562/580; 562/585
[58] Field of Search ................................ 562/580, 585

[56] References Cited

U.S. PATENT DOCUMENTS 3,202,705  8/1965  Powell ............................... 562/580
4,772,749  9/1988  Karrenbauer ....................... 562/580

FOREIGN PATENT DOCUMENTS 0324210  7/1989  European Pat. Off. .
0377430  7/1990  European Pat. Off. .
1290212  3/1962  France .
 868926  5/1961  United Kingdom .

OTHER PUBLICATIONS

Patent Abstracts of Japan, vol. 13, No. 315 (C-619)(3663), Jul. 18, 1989, & JP-A-01 102 033, Kimiaki Matsuda, "Removal of Organic Acid".

*Primary Examiner*—Paul J. Killos
*Attorney, Agent, or Firm*—Oblon, Spivak, McClelland, Maier & Neustadt

[57] ABSTRACT

A process for separating an organic acid or acids from an organic acid-containing solution obtained by a fermentation method in which glucose is used as starting material, which comprises contacting said organic acid-containing solution to a cation exchange resin to have the organic acid or acids adsorbed on the cation exchange resin, then contacting the cation exchange resin to an eluent to have the organic acid or acids desorbed, and then separating from the eluate a solution containing the organic acid or acids, wherein said organic acid-containing solution is contacted to the cation exchange resin under such a condition that the pH or the organic acid-containing solution is maintained at a pH level lower than pKa where Ka is the ionization constant of the organic acid or acids or the primary ionization constant in a case of a polybasic acid or acids, and the pH of the eluate is maintained at the above pH level.

8 Claims, 15 Drawing Sheets

PROCESS FOR SEPARATING AN ORGANIC ACID OR ACIDS FROM AN ORGANIC ACID-CONTAINING SOLUTION

The present invention relates to a process for separating an organic acid or acids from a solution containing such an acid or acids (hereinafter referred to simply as an organic acid-containing solution) obtained by a fermentation method in which glucose is used as starting material. More particularly, it relates to a process for efficiently separating e.g. tartaric acid, citric acid, lactic acid, gluconic acid or glycolic acid from an organic acid-containing solution such as a tartaric acid fermentation solution, a citric acid fermentation solution, a lactic acid fermentation solution, a gluconic acid fermentation solution or a glycolic acid fermentation solution obtained from glucose as starting material.

Heretofore, a process is known for producing an organic acid such as tartaric acid, citric acid, lactic acid, gluconic acid or glycolic acid by a fermentation method wherein glucose is used as starting material. To prevent a decrease in pH due to the organic acid formed as fermentation proceeds, calcium carbonate is used as a neutralizing agent. However, a calcium salt of an organic acid has low solubility and thus tends to precipitate, whereby the viscosity of the culture solution tends to increase. Further, when fermentation is conducted under an aerobic condition to form an organic acid, it tends to be difficult to stir and mix the culture medium and air due to the precipitation of the calcium salt. Further, in order to separate the organic acid from the formed calcium salt of the organic acid, the calcium salt of the organic acid is separated from the culture medium by e.g. filtration, and sulfuric acid is added thereto to separate the organic acid and calcium sulfate. Here, production of a large amount of calcium sulfate as by-product and deposition of boiler scale to the concentration boiler are problematic.

If sodium hydroxide is employed instead of calcium carbonate as the neutralizing agent in the culturing step, it is possible to avoid an increase in the viscosity of the culture medium. Even in such a case, calcium chloride, calcium hydroxide or the like is added to the supernatant of the culture medium to precipitate and separate the organic acid in the form of a calcium salt. Thus, like the case where calcium carbonate is employed as the neutralizing agent, there will be problems such as disposal treatment of by-product calcium sulfate and formation of boiler scale during the concentration operation.

As another method for separating the organic acid from the sodium salt of the organic acid formed by means of sodium hydroxide, there is a method which comprises contacting the supernatant containing the sodium salt of the organic acid to a strongly acidic cation exchange resin of Hydrogen type (hereinafter referred to as H type) to remove sodium ions. However, this method requires large amounts of the strongly acidic cation exchange resin of H type and hydrochloric acid or sulfuric acid for regenerating the cation exchange resin, and it has been difficult to practically use this method on an industrial scale.

On the other hand, Japanese Unexamined Patent Publication No. 191691/1989 filed by UOP Company (U.S. Pat. No. 4,720,579) discloses a method for separating an organic acid from inorganic salts directly by chromatography from a solution containing such an organic acid. As the separating agent, an adsorptive polymer such as a neutral polystyrene polymer or an anion exchange resin is used, and as a specific application, a method is known in which citric acid is separated from a fermentation solution. However, the selective adsorption of citric acid to such an adsorptive polymer is too strong that tailing tends to occur at the time of desorption by an eluent, whereby there has been a problem that a large amount of the eluent is required.

It is an object of the present invention to solve such problems inherent to the prior art and to provide a process for efficiently separating an organic acid or acids from a fermentation solution containing such an acid or acids together with saccharides, inorganic salts, colorant components, which fermentation solution is obtained by a fermentation method wherein glucose is used as starting material.

To accomplish the above object, the present inventors have studied a process wherein an organic acid-containing solution is permitted to flow through a column packed with a cation exchange resin to have organic acids adsorbed on the resin, and then an eluent is permitted to flow through the column packed with the acid-adsorbed resin to have the organic acids desorbed, followed by separation from the eluate a fraction containing the organic acids.

Components such as saccharides, inorganic salts and colorant components contained in the organic acid-containing solution obtained by a fermentation method are less absorbable on the cation exchange resin than the organic acid. Thus, they are readily desorbed by the flow-through of the eluent and elute substantially more quickly than the organic acids, whereby it is possible to separate a fraction containing organic acids as the main components. However, it has been found that when this method is carried out, part of organic acids could be converted to their salts. Since the adsorbability of such organic acid salts on the cation exchange resin is as low as inorganic salts, the organic acid salts readily elute together with the inorganic salts, whereby it is impossible to efficiently separate organic acids.

As a result of a further study to solve the above problem, it has been found that the partial change of the organic acids to the organic acid salts during the adsorption step by means of a cation exchange resin is attributable to the pH of the organic acid-containing solution during the adsorption treatment. Thus, it is possible to prevent the organic acids changing to their salts by maintaining the pH of the organic acid-containing solution at a level lower than a certain specific value during the adsorption treatment. On the basis of these discoveries, a further study has been conducted, and as a result, the present invention has been accomplished.

Thus, the present invention provides a process for separating an organic acid or acids from an organic acid-containing solution obtained by a fermentation method in which glucose is used as starting material, which comprises containing said organic acid-containing solution with a cation exchange resin to adsorb the organic acid or acids on the cation exchange resin, then contacting the cation exchange resin with an eluent to desorb the organic acid or acids, and then separating from the eluate a solution containing the organic acid or acids, wherein said organic acid-containing solution is contacted with the cation exchange resin under such a condition that the pH of the organic acid-containing solution is maintained at a pH level lower than pKa where Ka is the ionization constant of the organic acid or acids (or the primary ionization constant in a case of a polybasic acid or acids), and the pH of the eluate is maintained at the above pH level.

Figure 1:
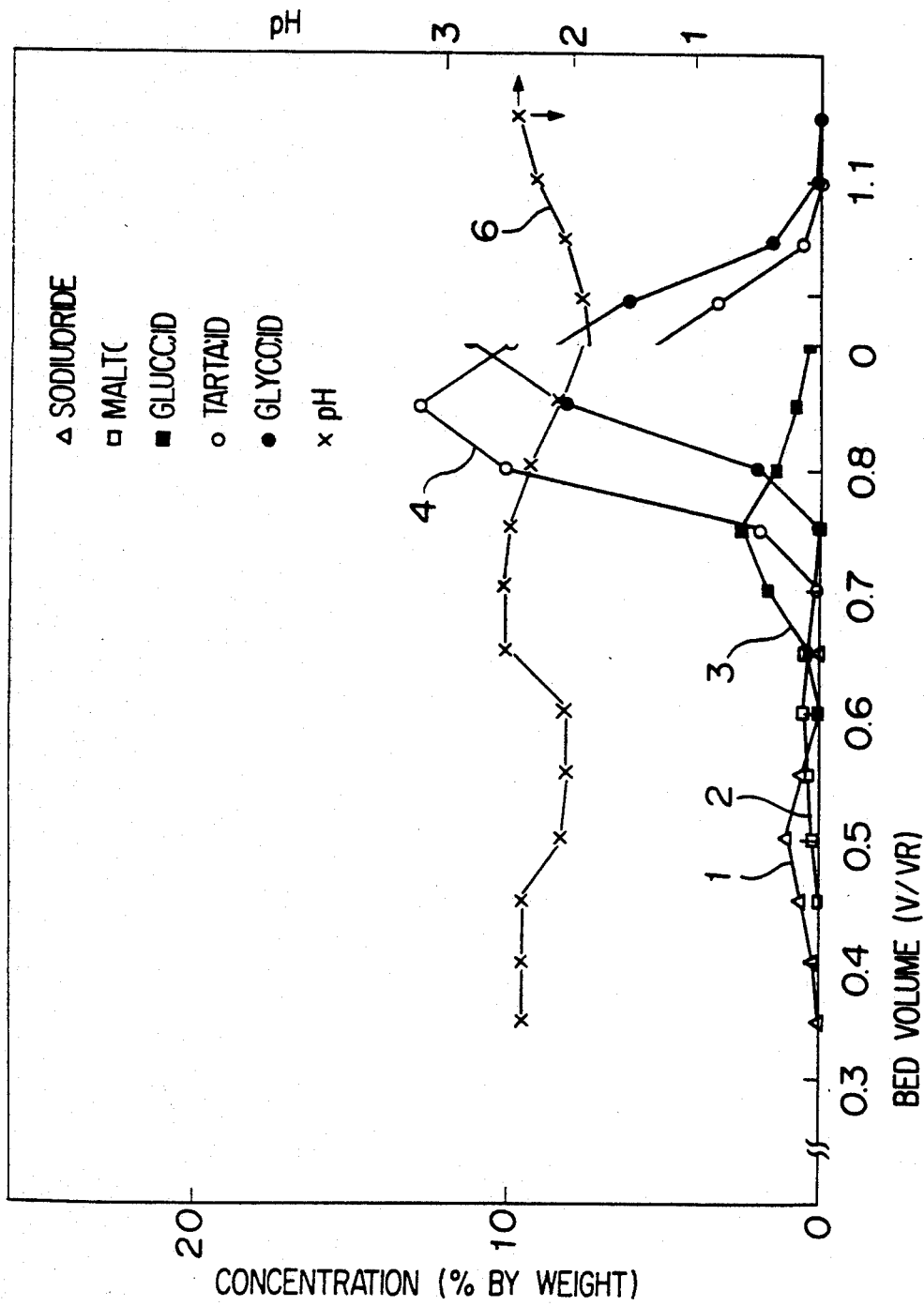
FIG. 1 is a graph showing the composition and the pH of the eluate in Example 1.

Now, the present invention will be described in detail with reference to the preferred embodiments.

The organic acid-containing solution obtained by a fermentation method wherein glucose is used as starting material, to be treated by the process of the present invention, may, for example, be a tartaric acid fermentation solution, a citric acid fermentation solution, a lactic acid fermentation solution, a gluconic acid fermentation solution or a glycolic acid fermentation solution. These organic acid-containing solutions contain various components in addition to the organic acids. For example, they contain polysaccharides and oligosaccharides which may be produced as by-products by the action of the bacteria, inorganic salts and colorant components. Further, depending upon the bacteria, a plurality of organic acids may be produced in many cases and intermediate products may also remain. Fermentation is conducted within a wide pH range depending upon the type of the bacteria. Therefore, part of organic acids are present in the form of their salts. Such a solution is treated by the present invention.

The cation exchange resin to be used in the process of the present invention, may be a well known strongly acidic cation exchange resin or weakly acidic cation exchange resin. It is preferred to employ a strongly acidic cation exchange resin of a divinylbenzene cross-linked polystyrene sulfonic acid type. The cross linking degree of divinylbenzene is usually at least 4% from the viewpoint of the physical strength of the resin and at most 10% from the viewpoint of the pore size of the resin particles. To improve the separating ability of the resin particles, the smaller the particle size and the sharper the particle size distribution, the better. However, if the particle size is too small, the pressure loss of the resin packed column during the passage of a liquid increases. Therefore, it is preferred to employ an average particle size of from 100 to 800 μm, preferably from 150 to 400 μm. Specific examples of the cation exchange resin include Diaion SK1B, Diaion UBK530, Diaion FRK01 and Diaion FRK31 (tradenames for the products of Mitsubishi Kasei Corporation); Lewatit S100, Lewatit S109, Lewatit SP112, Lewatit STW40 and Lewatit MSD1368 (trademarks for the products of Bayer Company); and Dowex HCR-S (trademark of the product of Dow Company). Among them, it is preferred to employ a cation exchange resin having a narrow particle size distribution such as Diaion UBK530 or Diaion FRK01, which is commercially available for chromatographic separation. Such a cation exchange resin is used in the form of a H type, an alkali metal type, an alkaline earth metal type or a mixed type thereof. For the separation between organic acids and inorganic acids, a Na type is superior to a H type, and for the separation between saccharides and organic acids, a Na type is superior to an alkaline earth metal type.

According to the process of the present invention, the above organic acid-containing solution obtained by a fermentation method, is contacted with a cation exchange resin to adsorb organic acids on the cation exchange resin, then the cation exchange resin is contacted with an eluent to desorb the organic acids and then from the eluate, a fraction containing the organic acids, is separated. In the present invention, it is essential that the pH of the organic acid-containing solution is maintained at a pH level lower than pKa where Ka is the ionization constant of the organic acid or acids (or the primary ionization constant in a case of a polybasic acid or acids), and the pH of the eluate is maintained at the above pH level. Namely, the pH of the organic acid or acids is required to be maintained at a low pH level in the column of the cation exchange resin. Even if the solution is introduced at a sufficiently low pH level, if the pH increases before it is eluted from the column outlet, the object of the present invention can not be achieved.

Namely, if the organic acid-containing solution is permitted to flow through the column packed with the cation exchange resin (hereinafter sometimes referred to as a separating agent) directly as it is by a conventional method, part of the organic acid will be converted to its salt, and such a salt has very low adsorbability to the separating agent (as low as inorganic salts), and thus elutes quickly together with the inorganic salts, whereby the organic acid can not efficiently be separated. Whereas, when the organic acid-containing solution and the cation exchange resin are contacted under such a condition that the pH of the organic acid-containing solution during the adsorption treatment is maintained at a pH level lower than pKa of the organic acid, and the pH of the eluate is maintained at the above pH level, the organic acid will not be converted to its salt, whereby the organic acid can efficiently be separated. When the organic acidcontaining solution contains two or more organic acids, the pH of the organic acid-containing solution during the adsorption treatment is maintained at a level lower than the pKa of the organic acid which has the lowest pKa.

To maintain the pH of the organic acid containing solution to a level lower than the pKa of the organic acid, firstly, an inorganic acid may, for example, be added to the organic acid-containing solution to adjust the pH to the desired level. However, if the pH of the organic acid-containing solution is already lower than the pKa of the organic acid, and the majority of the organic acid in the solution is in a free state, it is unnecessary to further lower the pH. Instead of adding an inorganic acid, part of the organic acid-containing solution may be passed through a column packed with a strongly acidic cation exchange resin of H type and the obtained solution may be mixed with the rest of the organic acid-containing solution to lower the pH. By such treatment, all the organic acid salt contained in the organic acid-containing solution will be converted to a free organic acid and an inorganic salt. The pH of the organic acid-containing solution is adjusted preferably within a range of 0.1 to 2.

With respect to the concentration of the organic acid containing solution, the higher, the better. However, if the concentration is too high, the viscosity will increase, and when it is passed through the column of the separating agent, the pressure loss of the separating agent-packed bed increases. Therefore, the concentration is usually within a range of from 10 to 80% by weight, preferably from 20 to 70% by weight. Here, the concentration is meant for the proportion of the dissolved solid component to the entire solution. In a case of an organic acid-containing solution having a large content of a hard component, it is advisable to neutralize it with e.g. sodium hydroxide in accordance with a conventional method, then to contact it with a weakly acidic cation exchange resin such as a cross-linked polymethacrylic acid of Na type to remove the hard component, and then to add an inorganic acid to adjust the pH to a level lower than the pKa of the organic acid.

The organic acid-containing solution having the pH adjusted as described above, is then passed through a column packed with the separating agent to have the organic acid adsorbed on the separating agent. Here, the pH of the eluate from the column is also required to be maintained at a level lower than the pKa of the organic acid. When the organic acid-containing solution is passed through the column, if the pH increases in the column to a level higher than the pKa of the organic acid, the organic acid will be converted to its salt, and such a salt has low adsorbability and will be eluted together with other inorganic salts or impurities. To maintain the pH of the eluate from the column to a level lower than the pKa of the organic acid, an inorganic acid solution may be passed through the column to adjust the pH of the solution in the column to a level lower than the pKa of the organic acid, prior to permitting the organic acid-containing solution to pass therethrough. It is preferred to preliminarily adjust the pH of the aqueous solution present in the space among the cation exchange resin particles to a low level, prior to the introduction of the organic acid-containing solution. Specifically, prior to the introduction of the organic acid-containing solution, an inorganic acid solution having a pH of from 0.1 to 2 may be passed through the column in an amount corresponding to the space volume of the packed layer. As the inorganic acid which may be used for adjusting the pH of the organic acid-containing solution or the solution in the separating agent-packed column, sulfuric acid, hydrochloric acid, nitric acid or phosphoric acid may, for example, be mentioned. Sulfuric acid is particularly preferred taking into consideration the corrosion of the apparatus or the influence to the crystallization step. Further, the acid concentration in the eluent may vary depending upon the pH of the organic acid-containing solution to be supplied to the column. Namely, if the pH of the organic acid-containing solution is sufficiently low, an aqueous inorganic acid solution of from $10^{-4}$ to 1 equivalent per l, preferably from $10^{-3}$ to 0.5 equivalent/l will be employed as the eluent. The temperature for passing the solution through the column is usually at least 0° C. to avoid freezing in the column packed with the separating agent and at most 100° C. to avoid the thermal deterioration of the separating agent and to avoid the thermal decomposition of the organic acid, and it is preferably within a range of from 10° to 80° C.

As described above, in the present invention, an organic acid-containing solution obtained by a fermentation method is passed through a separation column packed with a cation exchange resin to have the organic acid adsorbed on the resin, then an eluent is supplied to desorb the organic acid adsorbed on the resin, and from the eluate, an organic acid fraction is separated. The organic acid-containing solution obtained by a fermentation method, contains, in addition to the organic acid, various inorganic and organic acid salts, polysaccharides, oligosaccharides, glucose, colorant components, etc. These substances other than the organic acid have low adsorbability on the cation exchange resin and thus will readily be desorbed and quickly elute as an eluate. Firstly, inorganic salts, colorant components and polysaccharides having large molecular weights will elute, followed by oligosaccharides and further by glucose. Thereafter, free organic acids will elute sequentially in such an order that the one having small selective adsorbability elutes first. Therefore, by separating the eluate into two fractions i.e. before and after the initiation of the elution of the organic acid, it is possible to readily separate a preceding fraction containing inorganic salts, colorant components, polysaccharides, oligosaccharides and glucose, and a later fraction containing the desired free organic acid.

The fraction containing the free organic acid as the main component, thus obtained, has inorganic salts, colorant components and saccharides substantially removed and can be concentrated as it is to crystallize the organic acid. In a case where an organic acid of higher quality is required, the above fraction may further be treated with e.g. a strongly acidic cation exchange resin of H type to remove metal ions, then subjected to decoloring by means of e.g. active carbon, followed by concentration and crystallization to obtain an organic acid having a higher purity.

In the foregoing description and in the following Examples, the chromatographic operation is described with respect to a batch system separation method. However, the present invention is not limited to such a specific system. For example, it is possible to employ a batch system separation method as disclosed in e.g. Japanese Examined Patent Publication No. 24807/1970, Japanese Unexamined Patent Publication No. 149870/1978 (U.S. Pat. No. 4,267,054) or Japanese Unexamined Patent Publication No. 61903/1980 (U.S. Pat. No. 4,405,455), or a continuous separation method by a pseudo-moving bed system as disclosed in U.S. Pat. No. 2,985,589.

The process for separating an organic acid produced by a fermentation method of the present invention may be applied to various organic acids. It is preferably applied to an organic acid obtained by a fermentation method wherein glucose is used as starting material, such as tartaric acid, citric acid, lactic acid, gluconic acid or glycolic acid. As disclosed by Yamada et al. (Agr. Biol. Chem., Vol. 36, No. 8, p1,315-1,325, 1972), when tartaric acid is produced by a fermentation method using a tartaric acid-producing strain such as Gluconobacter sp., wherein glucose is used as starting material, tartaric acid and by-product glycolic acid will form as indicated by the following formation route.

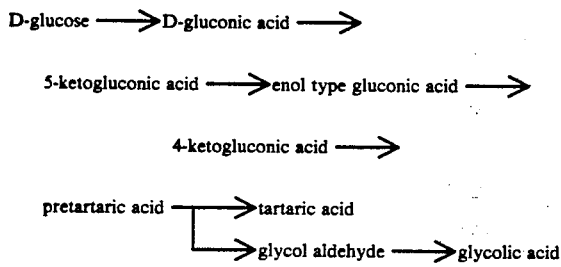

The above fermentation supernatant contains not only tartaric acid and glycolic acid but also gluconic acid, 5-ketogluconic acid, oligosaccharides, glucose, and various inorganic salts such as $NH_4Cl$, $KH_2PO_4$, $MgSO_4$, $MnSO_4$, NaCl and $Na_2SO_4$ which were added initially to the fermentation culture medium or formed by neutralization treatment after fermentation. Further, since the fermentation is conducted within a pH range of from 2 to 8, tartaric acid as well as by-product organic acids are partially present in the form of their salts. An organic acid-containing solution of this type is the solution to be treated by the present invention.

When the organic acid is tartaric acid, firstly inorganic salts, polysaccharides, oligosaccharides, glucose, colorant components, etc. (which have less adsorbability on the separating agent) are separated from the organic acid-containing fraction, and then separation of glycolic acid and tartaric acid is further conducted by a second separating agent column, whereby tartaric acid of higher purity can be obtained. Now, a specific manner for separating tartaric acid will be described.

For the separation of the above-mentioned tartaric acid fermentation solution, firstly the pH of the solution is adjusted to a level lower than $-\log_{10} Ka_1$ (pKa) 2.98 where $Ka_1$ is the primary ionization constant of tartaric acid to convert tartaric acid salts in the solution to free tartaric acid and inorganic salts. For the adjustment of the pH, hydrochloric acid, sulfuric acid, phosphoric acid or the like may be added. Otherwise, part of the solution may be contacted with a strongly acidic cation exchange resin of H type and then mixed with the rest of the solution to bring the pH to a level lower than 2.98. In a case where the pH of the solution is already lower than 2.98, it is unnecessary to further lower the pH. However, the pH is adjusted preferably to a level within a range of from 0.1 to 2. This tartaric acid-containing solution is introduced into a first separation column packed with a cation exchange resin to have an organic acid fraction containing tartaric acid adsorbed on the cation exchange resin. Then, an eluent is supplied to elute tartaric acid adsorbed on the separating agent to obtain a tartaric acid fraction. Inorganic salts, polysaccharides, oligosaccharides, glucose, colorant components, etc. flow out quickly as an eluate upon the supply of the eluent and thus can be separated and removed. The pH of the solution and the pH of the eluate are required to be maintained at a level lower than the pKa 2.98 of the tartaric acid. If the pH increases, part of tartaric acid will be converted to a tartaric acid salt, whereby the adsorbability will be low. Such tartaric acid salt will be desorbed together with other inorganic salts, whereby the recovery rate of tartaric acid tends to decrease. To avoid this, it is necessary to maintain the pH of the solution at a level lower than 2.98 and at the same time to maintain the pH of an aqueous solution present in the space in the separation column at a level lower than 2.98. It is preferred to preliminarily adjust the pH to such a low level, for example, by passing an inorganic acid solution through the separation column.

As the separating agent for the first separation column, it is preferred to employ a strongly acidic cation exchange resin of a divinylbenzene cross-linked polystyrene sulfonic acid type, wherein the proportion of the counter ion of the sulfonic acid group being a hydrogen ion is at most 70%. Such a cation exchange resin preferably has a H type proportion of at most 70%, more preferably at most 50%. Particularly preferred is such a cation exchange resin wherein H type is 0%, and the proportion of an alkali (or alkaline earth) metal type such as Na, K, Ca or Mg is 100%. With a view to separating saccharides and tartaric acid contained in the solution to be treated, an alkali metal type is preferred to the alkaline earth metal type.

When the tartaric acid containing solution is introduced into the first separation column packed with such a cation exchange resin and then an eluent is supplied, inorganic salts, colorant components, polysaccharides, oligosaccharides, glucose, etc. elute first and then various organic acids in their free state will flow out in such an order that the one having small selective adsorbability elutes first. By separating the eluate into two fractions i.e. before and after the initiation of elution of tartaric acid, it is possible to separate a preceding fraction containing salts, saccharides, colorant components and some impurity organic acids from a later fraction containing tartaric acid (hereinafter sometimes referred to simply as a tartaric acid fraction).

The tartaric acid fraction thus obtained has inorganic salts, colorant components, polysaccharides, oligosaccharides, glucose, etc. removed. Therefore, tartaric acid crystals can be obtained by subjecting the fraction directly to concentration and crystallization, or by treating it with a strongly acidic cation exchange resin of H type to remove metal ions present, then decoloring it by means of active carbon, followed by concentration and crystallization. However, to obtain tartaric acid crystals of higher purity, it is advisable to conduct separation of tartaric acid from coexisting other organic acids.

For example, in the fermentation solution obtained by aerobic fermentation of a tartaric acid-producing strain, by-product glycolic acid is contained in addition to tartaric acid. Therefore, even if such a fermentation solution is subjected to separation by the above first separation column, the glycolic acid will be contained in its entire amount in the tartaric acid fraction, and further separation of glycolic acid and tartaric acid will be required.

For this purpose, the tartaric acid fraction obtained from the first separation column is supplied to a second separation column to conduct the separation of tartaric acid and other organic acids. Namely, the pH of the solution is adjusted to a level of not higher than 2.98, if necessary, by adding an acid again to the tartaric acid fraction obtained from the first separation column and/or by contacting it with a strongly acidic cation exchange resin of H type, and the solution is then introduced into the second separation column packed with a cation exchange resin as a separating agent to have tartaric acid and other organic acids adsorbed on the separating agent. Then, an eluent is supplied to desorb tartaric acid and the organic acids adsorbed on the separating agent, and from the eluate, a fraction composed mainly of tartaric acid is separated.

As the separating agent for the second separation column, it is preferred to employ a cation exchange resin of a divinylbenzene cross-linked polystyrene sulfonic acid type wherein the proportion of the counter ion of the sulfonic group being a hydrogen ion is preferably at least 30%, more preferably at least 50% and most preferably 100%.

The pH of the organic acid-containing solution to be acceptable so long as it is not higher than 2.98. However, for the purpose of maintaining the proportion of H type as the counter ion of the sulfonic acid group for the second separation column at a high level, it is preferred to further lower the pH of the solution by an addition of an inorganic acid such as hydrochloric acid, sulfuric acid or phosphoric acid, or to lower the metal ion concentration in the solution and then supply the solution to the separation column, whereby the separating performance of the separating agent can be maintained at a high level.

The eluent, the type and concentration of the inorganic acid, the eluent, the temperature of the solution to be passed through the column, the concentration of the organic acid-containing solution, etc., may be set commonly for both the first and second separation columns.

As described above, the tartaric acid fraction obtained from the first column is supplied to the second column to have tartaric acid adsorbed on the separating agent, and then an eluent is supplied to desorb the tartaric acid adsorbed on the separating agent to obtain a tartaric acid fraction again. The purity of tartaric acid in the dissolved solid component contained in the tartaric acid fraction obtained from this second separation column is much higher than the purity of the tartaric acid fraction obtained from the first separation column. Accordingly, by subjecting the tartaric acid fraction from the second separation column to a concentration and crystallization operation, it is possible to obtain tartaric acid crystals of very high purity.

Now, the present invention will be described in further detail with reference to Examples. However, it should be understood that the present invention is by no means restricted to such specific Examples. In the following Examples and Comparative Examples, "%" means "% by weight" unless otherwise specified.

EXAMPLE 1

According to a literature (Toru Kodama, Uichiro Kotera and Koichi Yamada; Fermentation Technology, Vol. 49, No. 2, p93-97, 1971), a tartaric acid-producing strain *Gluconobacter suboxydans* 2026Y2 strain was inoculated to 50 ml of a culture medium of pH 6.0 (composition: 100 g/l of glucose, 1 g/l of $KH_2PO_4$, 0.25 g/l of $MgSO_4\cdot7H_2O$, 0.1 g/l of $NH_4VO_3$, 20 g/l of $CaCO_3$) in a 500 ml flask and cultured under shaking (amplitude: 70 mm, 128 reciprocations/min) at 26° C. for 6 days. The pH of the culture medium was 2.8, and 8.4 g/l of tartaric acid, 1.0 g/l of intermediate product 5-ketogluconic acid, and 21 g/l of by-product 2-ketogluconic acid were detected. In order to subject this fermentation solution to chromatographic separation, it is necessary to filter off suspended substances in the culture medium, then treat calcium salts of dissolved organic acids by an ion exchange resin for softening, then concentrate the solution, thereafter add sulfuric acid to adjust the pH to a level lower than the $pKa_1$(2.98) of tartaric acid, and then supply the solution to a Chromatographic separation column. In this Example, however, to grasp the behavior of an inorganic salt in the culture medium and the behavior of an unreacted saccharide, it was decided to prepare a makeup solution by adding NaCl and maltose or glucose as the respective model components, gluconic acid as an intermediate product of tartaric acid, and glycolic acid as a by-product, to tartaric acid.

Namely, a mixture comprising 1.9% of sodium chloride, 1.5% of maltose, 7.5% of gluconic acid (pKa: 3.60), 47.5% of tartaric acid (pKa: 2.98) and 41.6% of glycolic acid (pKa: 3.83), was dissolved in water to obtain an aqueous solution having a concentration of 46.7%. Then, concentrated sulfuric acid was added thereto to obtain an organic acid-containing solution having pH 0.71.

On the other hand, 150 ml of a strongly acidic cation exchange resin Diaion UBK530 (Na type) was packed as a separating agent to a separation column (inner diameter: 18 mm, length: 600 mm), and from the top of the column, 150 ml of a 0.1% dilute sulfuric acid aqueous solution (pH: 1.7) was permitted to flow through the column so that the pH of the eluate from the bottom became lower than the pKa (2.98) of tartaric acid, which is the smallest among the pKa of the above three types of organic acids.

Then, 10% by volume, based on the volume of the separating agent, (15 ml) of the above organic acid-containing solution was introduced from the top of the column and permitted to flow at a flow rate of 84 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 1.

In FIG. 1, the ordinate on the left hand side indicates the concentration (% by weight) of each component in the eluate, the ordinate on the right hand side indicates the pH of the eluate, and the abscissa indicates a ratio (V/VR) of the volume (V) of the eluate to the volume (VR) of the separating agent. In the following description, this volume ratio will be referred to as a bed volume (V/VR).

As shown in FIG. 1, the pH of the eluate was maintained to be always lower than the primary ionization constant (pKa: 2.98) of tartaric acid. Further, by separating the eluate into two fractions i.e. the preceding fraction and the later fraction with the separating point being at a bed volume (V/VR) of 0.7, it was possible to readily separate a fraction containing mainly the inorganic salt (sodium chloride), the oligosaccharide (maltose) and part of gluconic acid as the preceding fraction and an organic acid fraction containing tartaric acid and glycolic acid as the main components, as the later fraction.

EXAMPLE 2

In accordance with the literature cited in Example 1, a makeup solution was prepared by adding the respective model components to tartaric acid in order to grasp the behavior of an inorganic salt in the culture medium and the behavior of an unreacted saccharide.

Namely, a mixture comprising 2.1% of sodium chloride, 1.7% of maltose, 7.9% of gluconic acid (pKa: 3.60), 45.5% of tartaric acid (pKa: 2.98) and 42.8% of glycolic acid (pKa: 3.83), was dissolved in water to obtain an aqueous solution having a concentration of 51.7%. Then, concentrated sulfuric acid was added thereto to obtain an organic acid-containing solution having pH 0.73.

On the other hand, 150 ml of Diaion UBK530 (Na/H type ratio: 70/30) was packed in the same separation column as used in Example 1, and from the top of the column, 150 ml of a 0.1% dilute sulfuric acid aqueous solution (pH: 1.7) was permitted to flow so that the pH of the eluate from the bottom became lower than the pKa (2.98) of tartaric acid, which is the smallest among the pKa of the above three types of organic acids.

Then, 10% by volume, based on the volume of the separating agent, (15 ml) of the above organic acid-containing solution was permitted to flow from the top of the column at a flow rate of 76.5 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 2.

Figure 2:
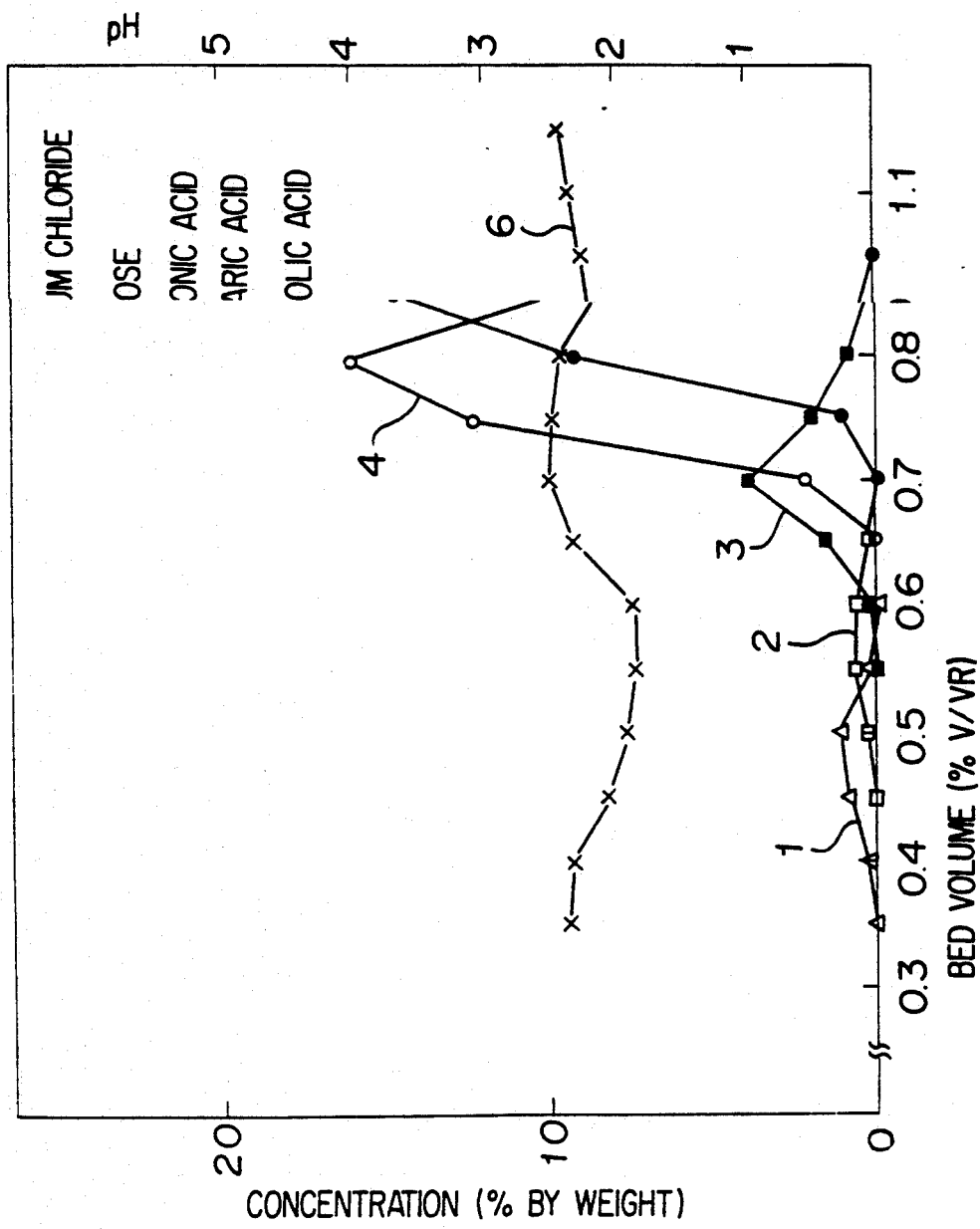
FIG. 2 is a graph showing the composition and the pH of the eluate in Example 2.

As shown in FIG. 2, the pH of the eluate was maintained to be always lower than the primary ionization constant (pKa: 2.98) of tartaric acid. Further, by separating the eluate into two fractions i.e. the preceding fraction and the later fraction with the separation point being at a bed volume (V/VR) of 0.65, it was possible to readily separate a fraction containing mainly the inorganic salt (sodium chloride) and the oligosaccharide (maltose) and an organic acid fraction containing tartaric acid and glycolic acid as the main components.

EXAMPLE 3

In the same manner as in Example 2, a makeup solution was prepared as follows.

A mixture comprising 2.2% of sodium chloride, 1.8% of maltose, 7.5% of gluconic acid (pKa: 3.60), 44.9% of tartaric acid (pKa: 2.98) and 43.6% of glycolic acid (pKa: 3.83), was dissolved in water to obtain an aqueous solution having a concentration of 50%. Then, concentrated sulfuric acid was added thereto to obtain an organic acid-containing solution having pH 0.69.

On the other hand, 150 ml of Diaion UBK530 (Na/H type ratio: 30/70) was packed in the same separation column as used in Example 1, and from the top of the column, 150 ml of a 0.1% dilute sulfuric acid aqueous solution (pH: 1.7) was permitted to flow so that the pH of the eluate from the bottom became lower than the pKa (2.98) of tartaric acid, which is the smallest among the pKa of the above three types of organic acids.

Then, 10% by volume, based on the volume of the separating agent (15 ml) of the above organic acid-containing solution was permitted to flow from the top of the column at a flow rate of 84 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 3.

Figure 3:
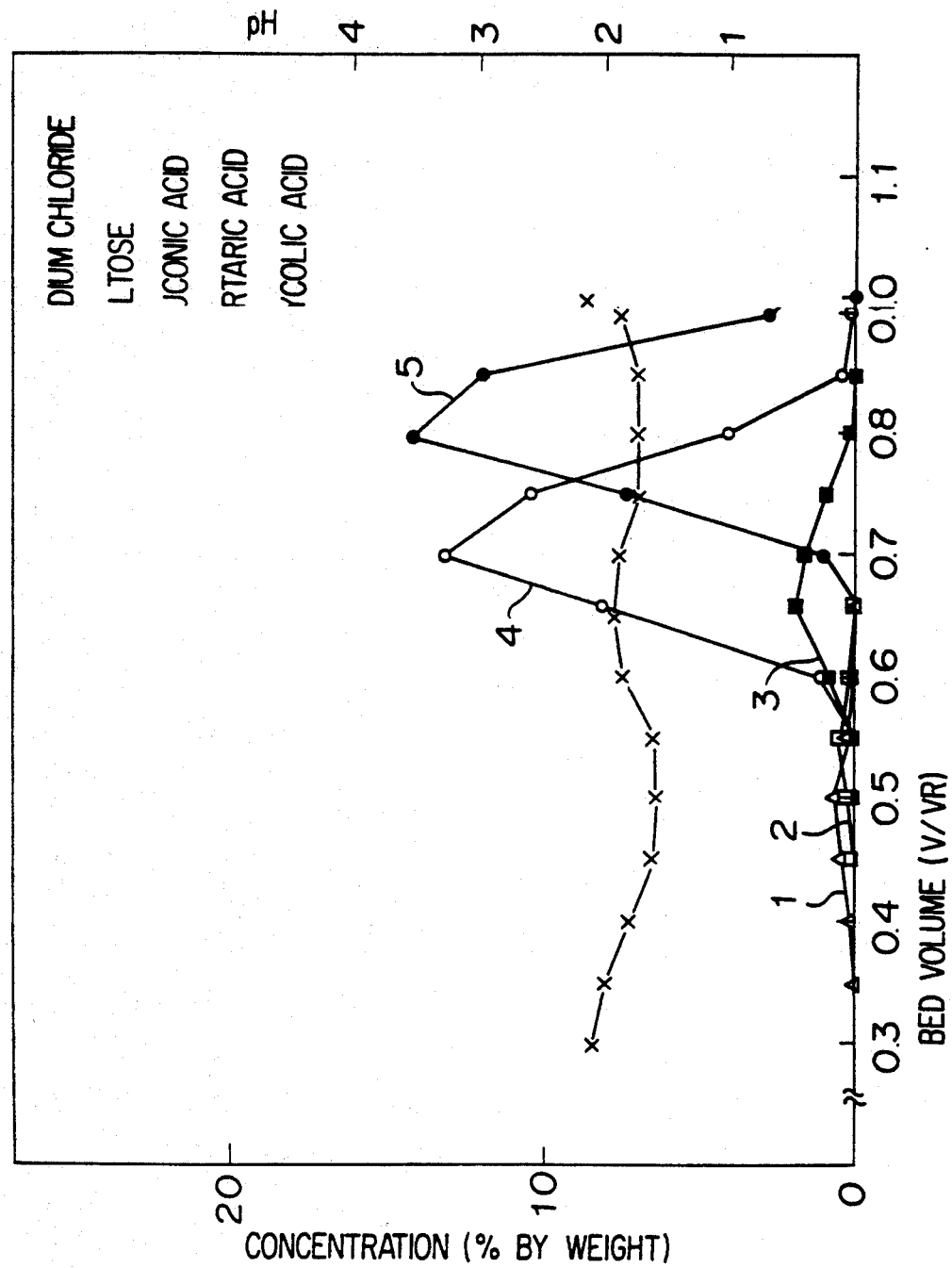
FIG. 3 is a graph showing the composition and the pH of the eluate in Example 3.

As shown in FIG. 3, the pH of the eluate was maintained to be always lower than the primary ionization constant (pKa: 2.98) of tartaric acid. Further, by separating the eluate into two fractions i.e. the preceding fraction and the later fraction with the separating point being at a bed volume (V/VR) of 0.60, it was possible to readily separate a fraction containing mainly the inorganic salt (sodium chloride) and the oligosaccharide (maltose) and an organic acid-fraction containing tartaric acid and glycolic acid as the main components.

EXAMPLE 4

Gluconobacter suboxydans strain was inoculated to 0.4 l of a sterilized culture medium (composition: 150 g/l of glucose, 5 g/l of corn steep liquor, 1.85 g/l of $(NH_4)_2SO_4$, 1.0 g/l of $KH_2PO_4$, 0.25 g/l of $MgSO_4 \cdot 7H_2O$, 0.048 g/l of $MnSO_4 \cdot 5H_2O$, 0.15 g/l of $NH_4VO_3$, 30 g/l of $CaCO_3$, pH: 6.5) in a 1 l jar and cultured for five days at a stirring speed of 1,200 rpm at an air supply rate of 1 V/VM at 27° C. Upon completion of the culturing, the culture solution was filtered to remove suspended substances, and to the supernatant thereby obtained, glycolic acid, tartaric acid, gluconic acid and their salts, sodium sulfate and maltose were added, and sulfuric acid was added to bring the pH to 1.68, and the organic acid-containing solution thereby obtained was analyzed. As a result, the composition was found to be 24.4% of sodium sulfate, 6.2% of maltose, 5.3% of gluconic acid (pKa: 3.60), 34.4% of tartaric acid (pKa: 2.98) and 30.0% of glycolic acid (pKa: 3.83), and the concentration was 42%.

On the other hand, 130 ml of Diaion UBK530 (Na type) was packed in the same separation column as used in Example 1, and from the top of the column, 130 ml of a 0.1% dilute sulfuric acid aqueous solution (pH: 1.7) was permitted to flow, so that the pH of the eluate from the bottom became lower than the pKa (2.98) of tartaric acid, which was the smallest among the pKa of the above three types of organic acids.

Then, 13 ml of the above organic acid-containing solution was permitted to flow from the top of the column at a flow rate of a 65 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 4.

Figure 4:
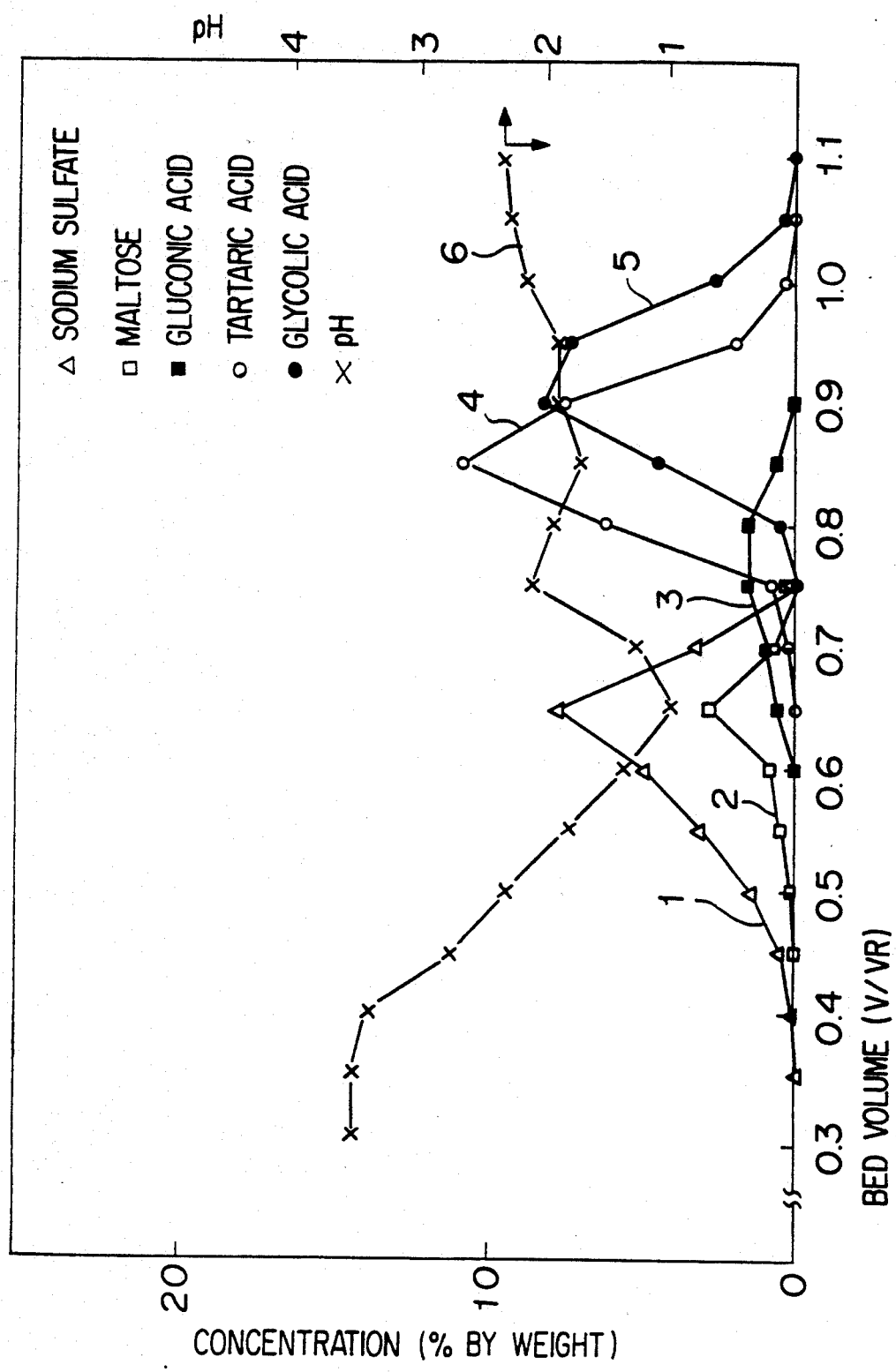
FIG. 4 is a graph showing the composition and the pH of the eluate in Example 4.

As shown in FIG. 4, the pH of the eluate was maintained to be always lower than the primary ionization constant (pKa: 2.98) of tartaric acid. Further, by separating the eluate into two fractions i.e. the preceding fraction and the later fraction with the separating point being at a bed volume (V/VR) of 0.75, it was possible to readily separate a fraction containing mainly the inorganic salt (sodium sulfate) and the oligosaccharide (maltose) and part of gluconic acid, and an organic acid fraction containing tartaric acid and glycolic acid as the main components.

EXAMPLE 5

To the supernatant of the culture medium obtained in Example 4, glycolic acid, tartaric acid, gluconic acid and their salts, sodium sulfate and maltose were added, and sulfuric acid was further added thereto to bring the pH to 1.70. The organic acid-containing solution thereby obtained was analyzed. As a result, its composition was found to be 23.1% of sodium sulfate, 7.7% of maltose, 4.1% of gluconic acid (pKa: 3.60), 34.7% of tartaric acid (pKa: 2.98), and 30.4% of glycolic acid (pKa: 3.83), and the concentration was 47.5%.

On the other hand, 130 ml of diaion UBK530 (Mg type) was packed in the same separation column as used in Example 1, and from the top of the column, 130 ml of a 0.1% dilute sulfuric acid aqueous solution (pH: 1.7) was permitted to flow so that the pH of the eluate from the bottom became lower than the pKa (2.98) of tartaric acid, which was the smallest among the pKa of the above three types of organic acids.

Then, 13 ml of the above organic acid-containing solution was permitted to flow from the top of the column at a flow rate of 65 ml/hr at a temperature of 35° C., and then 0.1% sulfuric acid aqueous solution was permitted to flow as an eluent at the same temperature and the same flow rate, whereupon the composition and the pH of the eluate from the bottom of the column were measured. The results are shown in FIG. 5.

Figure 5:
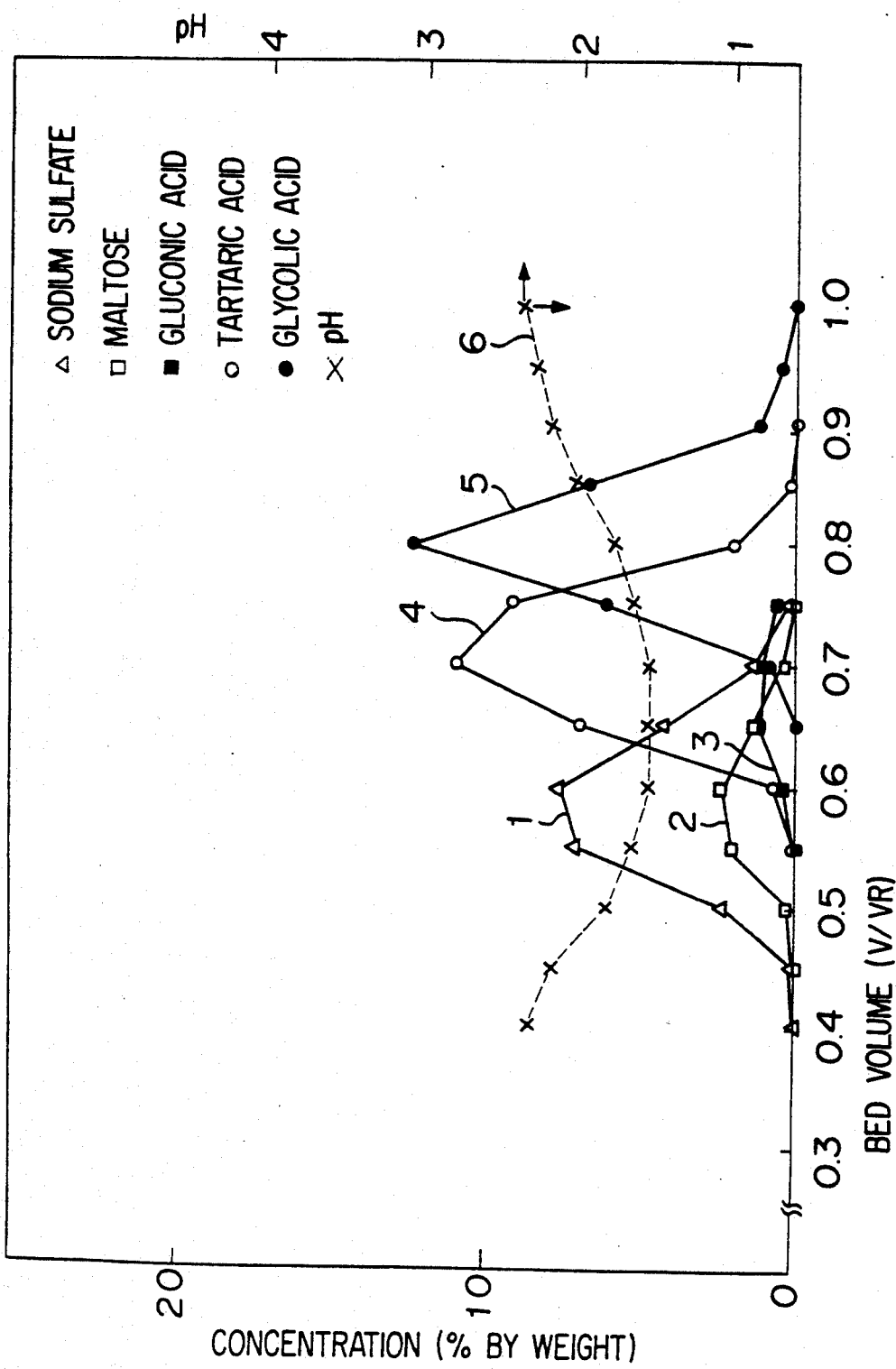
FIG. 5 is a graph showing the composition and the pH of the eluate in Example 5.

As shown in FIG. 5, the pH of the eluate was maintained to be always lower than the primary ionization constant (pKa: 2.98) of tartaric acid. Further, by separating the eluate into two fractions i.e. the preceding fraction and the later fraction with the separating point being at a bed volume (V/VR) of 0.675, it was possible to readily separate a fraction containing mainly the inorganic salt (sodium sulfate) and the oligosaccharide (maltose) and part of gluconic acid, and an organic acid fraction containing tartaric acid and glycolic acid as the main components.

EXAMPLE 6

In the same manner as in Example 2, a makeup solution was prepared as follows.

A mixture comprising 1.9% of sodium chloride, 1.9% of maltose, 6.8% of gluconic acid (pKa: 3.60), 49.6% of tartaric acid (pKa: 2.98) and 39.8% of glycolic acid (pKa: 3.83), was dissolved in water to obtain an aqueous solution having a concentration of 22.6%. Then, concentrated sulfuric acid was added thereto to obtain an organic acid-containing solution having pH 0.89.

On the other hand, 130 ml of Diaion FRK31 (Na type) was packed in the same separation column as used in Example 1, and from the top of the column, 400 ml of a 0.1% dilute sulfuric acid aqueous solution (pH: 1.7) was allowed to flow so that the pH of the eluate from the bottom became lower than the pKa (2.98) of tartaric acid, which was the smallest among the pKa of the above three types of organic acids.

Then, 13 ml of the above organic acid-containing solution was permitted to flow from the top of the column at a flow rate of 70 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 6.

Figure 6:
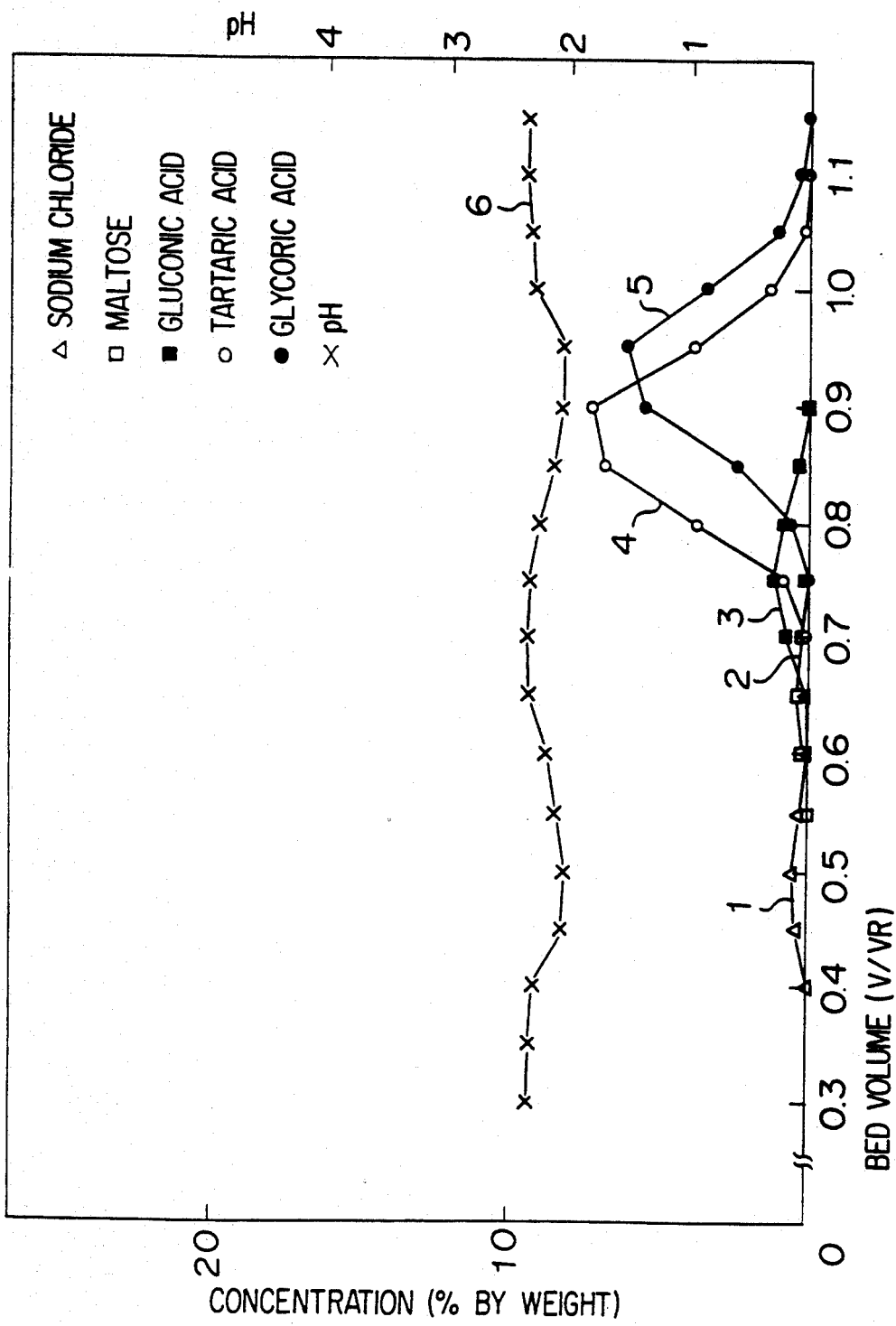
FIG. 6 is a graph showing the composition and the pH of the eluate in Example 6.

As shown in FIG. 6, the pH of the eluate was maintained to be always lower than the primary ionization constant (pKa: 2.98) of tartaric acid. Further, by separating the eluate into two fractions i.e. the preceding fraction and the later fraction with the separation point being at a bed volume (V/VR) of 0.75, it was possible to readily separate a fraction containing mainly the inorganic salt (sodium chloride) and the oligosaccharide (maltose), and an organic acid-fraction containing tartaric acid and glycolic acid as the main components.

EXAMPLE 7

According to a literature (Ping Shu and Marvin J. Johnson; Industrial and Engineering Chemistry, Vol. 40, p1,202–1,205, 1948), a citric acid-producing strain *Aspergillus niger* ATCC 1015 strain was inoculated to 50 ml of a culture medium adjusted to pH 3.8 (composition: 145 g/l of sucrose, 2.5 g/l of $KH_2PO_4$, 0.25 g/l of $MgSO_4 \cdot 7H_2O$, 2.5 g/l of $NH_4NO_3$, 0.06 mg/l of $Cu^{++}$, 0.25 mg/l of $Zn^{++}$, 1.3 mg/l of $Fe^{++}$, 1.0 mg/l of $Mn^{++}$) in a 500 ml Erlenmeyer flask, and cultured at 25° C. under rotational shaking at a rotational speed of 270 rpm. Nine days later, 91 g/l of citric acid was obtained. The amount of the bacteria was 1.8 g/l, and the remaining sucrose was 0.3 g/l. In order to subject this fermentation solution to chromatographic separation, it is necessary to separate the bacterial cells from the culture medium, concentrate the solution and then supply the solution to a chromatographic separation column. However, in this Example, in order to grasp the behavior of an inorganic salt in the culture medium and the behavior of an unreacted saccharide, a makeup solution was prepared by adding $Na_2SO_4$ and maltose as the respective model components.

Sulfuric acid was added to an aqueous solution containing citric acid (pKa: 3.09) and its salt, sodium sulfate and maltose to bring the pH to 1.56. The organic acid-containing solution thus obtained was analyzed. As a result, the composition was found to be 49.3% of sodium sulfate, 2.9% of maltose and 47.8% of citric acid, and the concentration was 50.4%.

On the other hand, 130 ml of Diaion UBK530 (Na type) was packed into the same separation column as used in Example 1, and from the top of the column, 130 ml of a 0.1% dilute sulfuric acid aqueous solution (pH: 1.7) was permitted to flow so that the pH of the eluate from the bottom became smaller than the pKa (3.09) of the organic acid.

Then, 13 ml of the above organic acid-containing solution was permitted to flow from the top of the column at a flow rate of 65 ml/hr at a temperature of 35° C., and then a 0.1% sulfuric acid aqueous solution was permitted to flow as an eluent at the same temperature and the same flow rate, whereupon the composition and the pH of the eluate from the bottom were measured. The results are shown in FIG. 7.

Figure 7:
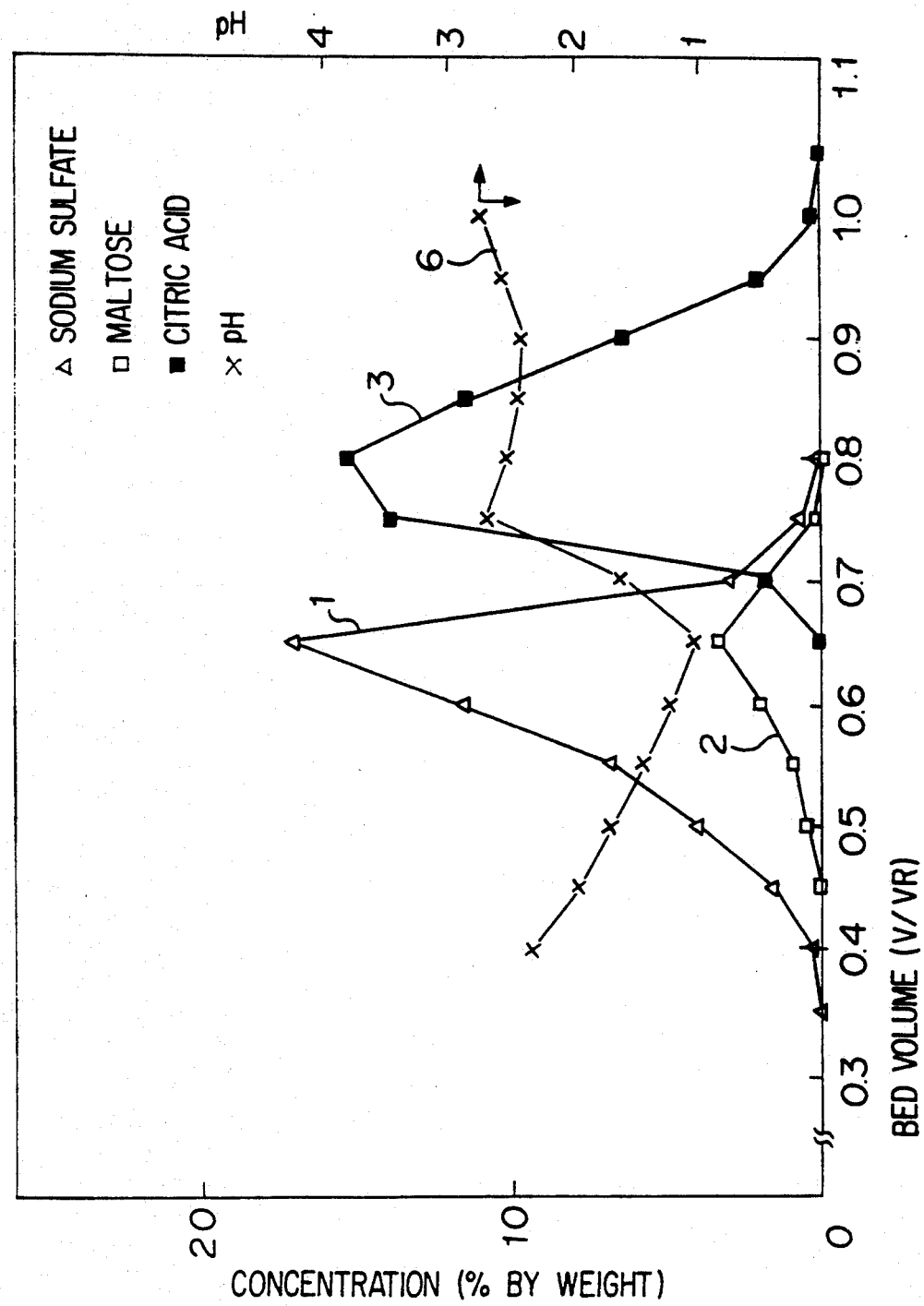
FIG. 7 is a graph showing the composition and the pH of the eluate in Example 7.

As shown in FIG. 7, the pH of the eluate was maintained to be always lower than the ionization constant (pKa: 3.08) of citric acid. Further, by separating the eluate into two fractions i.e. the preceding fraction and the later fraction with the separating point being at a bed volume (V/VR) of 0.7, it was possible to readily separate a fraction containing mainly the inorganic salt (sodium sulfate) and the oligosaccharide (maltose), and an organic acid-containing fraction containing citric acid as the main component.

EXAMPLE 8

According to a literature (Morton R. Friedman and Elmer L. Garden, Jr.: Biotechnology and Bioengineering, Vol 12, p961–974, 1970), a lactic acid-producing strain *Lactobacillus delbrueckii* was inoculated to 2 l of a culture medium comprising 10% of glucose, 6% of Yeast extract, 0.6 g/l of $MgSO_4$, 0.03 g/l of $FeSO_4$, 0.03 g/l of $MnSO_4$, 1.0 g/l of sodium acetate, 0.5 g/l of $K_2HPO_4$ and 0.5 g/l of $KH_2PO_4$, and batch culturing was conducted in a 4 l jar at 42° C. in an atmosphere of nitrogen under stirring at a rotational speed of 500 rpm while adjusting the pH to pH 5.8 with NaOH. In 19 hours, glucose was consumed, and a mixture of lactic acid and sodium lactate was obtained. The total lactic acid concentration at that time was 71 g/l. In order to subject this fermentation solution to chromatographic separation treatment, it is necessary to separate bacterial cells from the culture medium, add sulfuric acid to the supernatant, lower the pH to a level lower than the pKa 3.87 of lactic acid to obtain a mixture comprising sodium sulfate as the main inorganic salt and lactic acid and then concentrate the solution. However, in this Example, on the basis of the above culture medium, a makeup solution was prepared to grasp the behaviors of lactic acid and sodium sulfate in the chromatographic separation.

Sulfuric acid was added to an aqueous solution containing lactic acid (pKa: 3.87) and its salt and sodium sulfate to adjust the pH to 1.60. The organic acid-containing solution thereby obtained was analyzed. As a result, its composition was found to be 25.1% of sodium sulfate and 74.9% of lactic acid, and the concentration was 38%.

On the other hand, 130 ml of Diaion UBK530 (Na type) was packed into the same separation column as used in Example 1, and from the top of the column, 130 ml of a 0.1% dilute sulfuric acid aqueous solution (pH: 1.7) was permitted to flow so that the pH of the eluate from the bottom became lower than the pKa (3.09) of the organic acid.

Then, 13 ml of the above organic acid-containing solution was permitted to flow from the top of the column at a flow rate of 66 ml/hr at a temperature of 35° C., and then a 0.1% sulfuric acid aqueous solution was permitted to flow as an eluent at the same temperature and the same flow rate, whereupon the composition and the pH of the eluate from the bottom were measured. The results are shown in FIG. 8.

Figure 8:
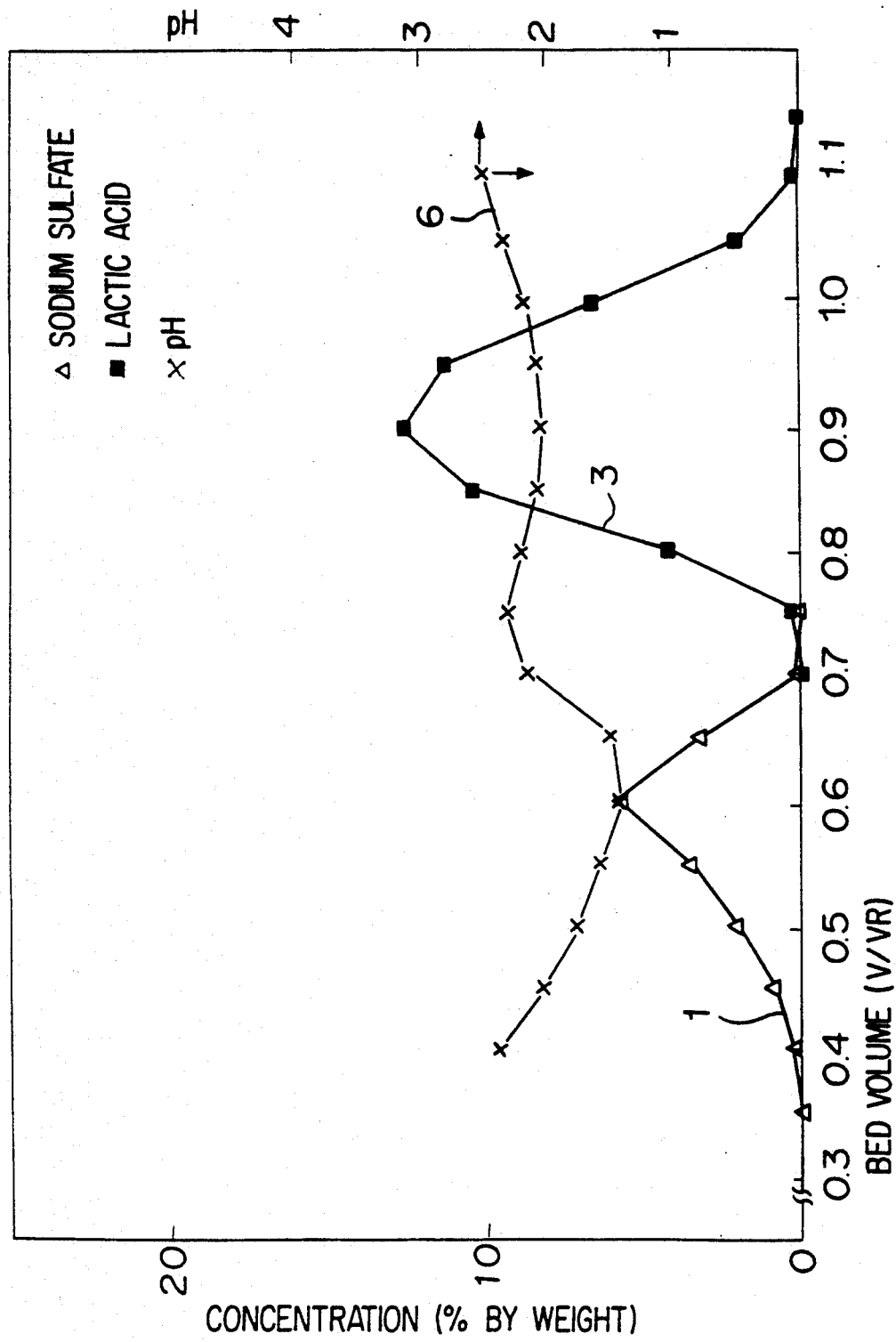
FIG. 8 is a graph showing the composition and the pH of the eluate in Example 8.

As shown in FIG. 8, the pH of the eluate was maintained to be always lower than the ionization constant (pKa: 3.87) of lactic acid. Further, by separating the eluate into two fractions i.e. the preceding fraction and the later fraction with the separating point being at a bed volume (V/VR) of 0.725, it was possible to readily separate a fraction containing the inorganic salt (sodium sulfate), and an organic acid-containing fraction containing lactic acid.

COMPARATIVE EXAMPLE 1

In the same manner as in Example 2, a makeup solution was prepared as follows.

A mixture comprising 1.9% of sodium chloride, 1.8% of glucose, 5.8% of gluconic acid (pKa: 3.60), 45.5% of tartaric acid (pKa: 2.98) and 45.0% of glycolic acid (pKa: 3.83), was dissolved in water to obtain an aqueous solution having a concentration of 50.3%. Then, concentrated sulfuric acid was added thereto to obtain an organic acid-containing solution having pH 0.69.

Figure 9:
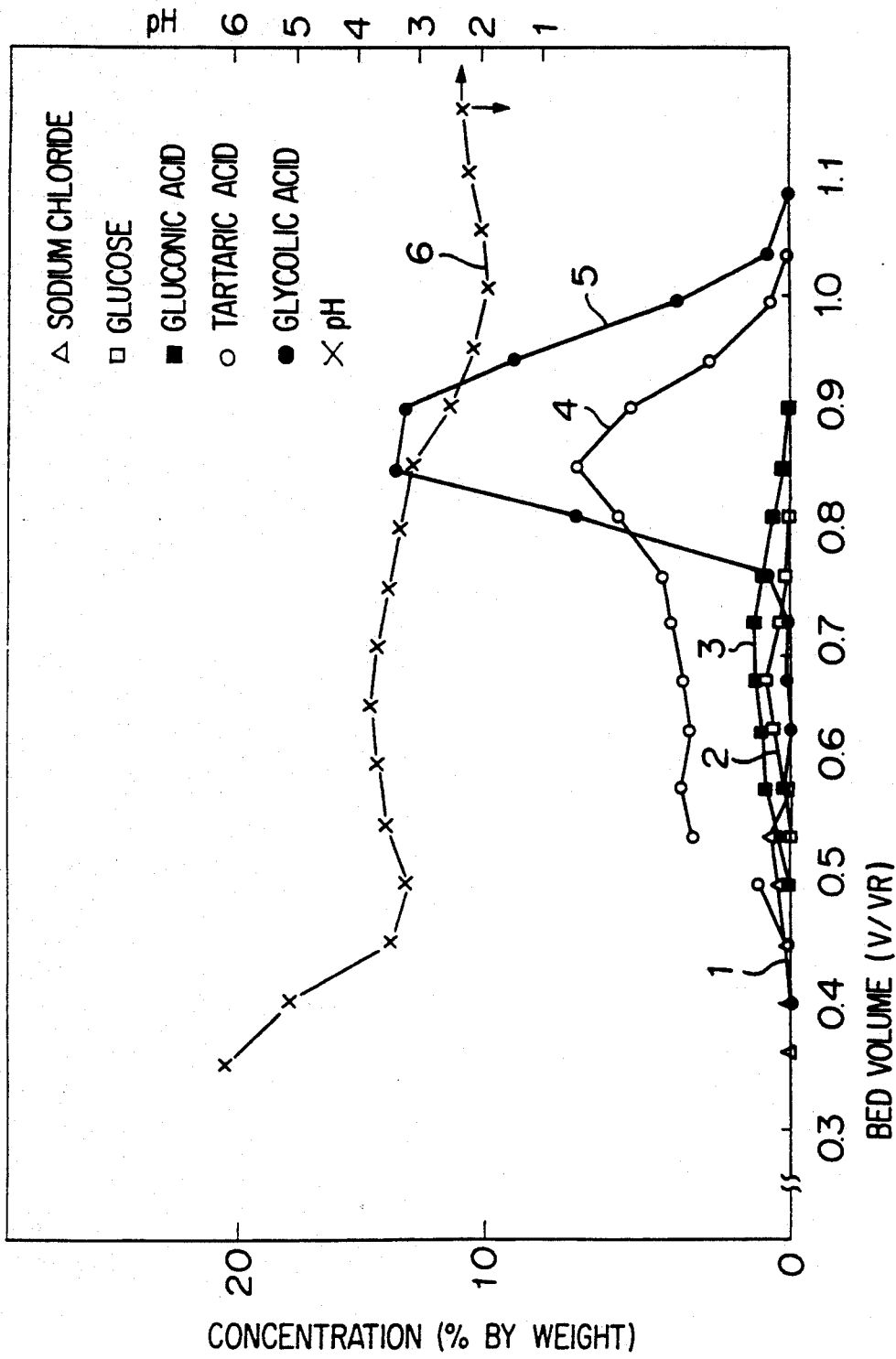
FIG. 9 is a graph showing the composition and the pH of the eluate in Comparative Example 1.

On the other hand, 167 ml of Diaion UBK530 (Na type) was packed in a separation column (inner diameter: 18 mm, length: 660 mm), and then water was permitted to flow therethrough to adequately wash the column. Then, 13 ml of the above organic acid-containing solution was permitted to flow from the top of the column at a flow rate of 84 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 9.

In Comparative Example 1, the column packed with the separating agent was subjected to washing with water only without passing a 0.1% sulfuric acid aqueous solution therethrough, and then the above organic acid-containing solution was permitted to flow through this column. Therefore, the pH (0.69) of the organic acid-containing solution became higher in the column than the pKa (2.98) of tartaric acid, whereby part of tartaric acid in the organic acid-containing solution was converted to a tartaric acid salt. Such a tartaric acid salt and sodium chloride start to elute substantially simultaneously at a bed volume (V/VR) of about 0.4, and therefore it is difficult to separate the two. On the other hand, gluconic acid and glycolic acid having pKa larger than tartaric acid are less likely to form organic acid salts, and therefore they are not substantially affected. However, with a view to separating a fraction containing mainly organic acids and a fraction containing inorganic salts and saccharides, this shows that it is important to preliminarily adjust the pH of the solution in the separation column and the pH of the eluate to a level lower than the pKa of the organic acid (tartaric acid) which has the smallest pKa in the organic acid-containing solution, when the organic acid-containing solution is to be introduced into the separation column.

EXAMPLE 9

To the supernatant of the culture medium obtained in Example 4, glycolic acid, tartaric acid, gluconic acid and their salts, sodium sulfate and maltose were added, and sulfuric acid was further added thereto to bring the pH to 1.68. The organic acid-containing solution thereby obtained, was analyzed. As a result, its composition was found to be 24.4% of sodium sulfate, 6.2% of maltose, 5.3% of gluconic acid (pKa: 3.60), 34.4% of tartaric acid (pKa: 2.98) and 30.0% of glycolic acid (pKa: 3.83), and the concentration was 42%.

On the other hand, 130 ml of Diaion UBK530 (Na type) was packed in the same separation column as used in Example 1, and from the top of the column, 130 ml of a 0.1% dilute sulfuric acid aqueous solution (pH: 1.7) was permitted to flow so that the pH of the eluate from the bottom became lower than the pKa (2.98) of tartaric acid, which is the smallest among the pKa of the above three types of organic acids.

Then, 13 ml of the above organic acid-containing solution was permitted to flow from the top of the column at a flow rate of 65 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 10.

Figure 10:
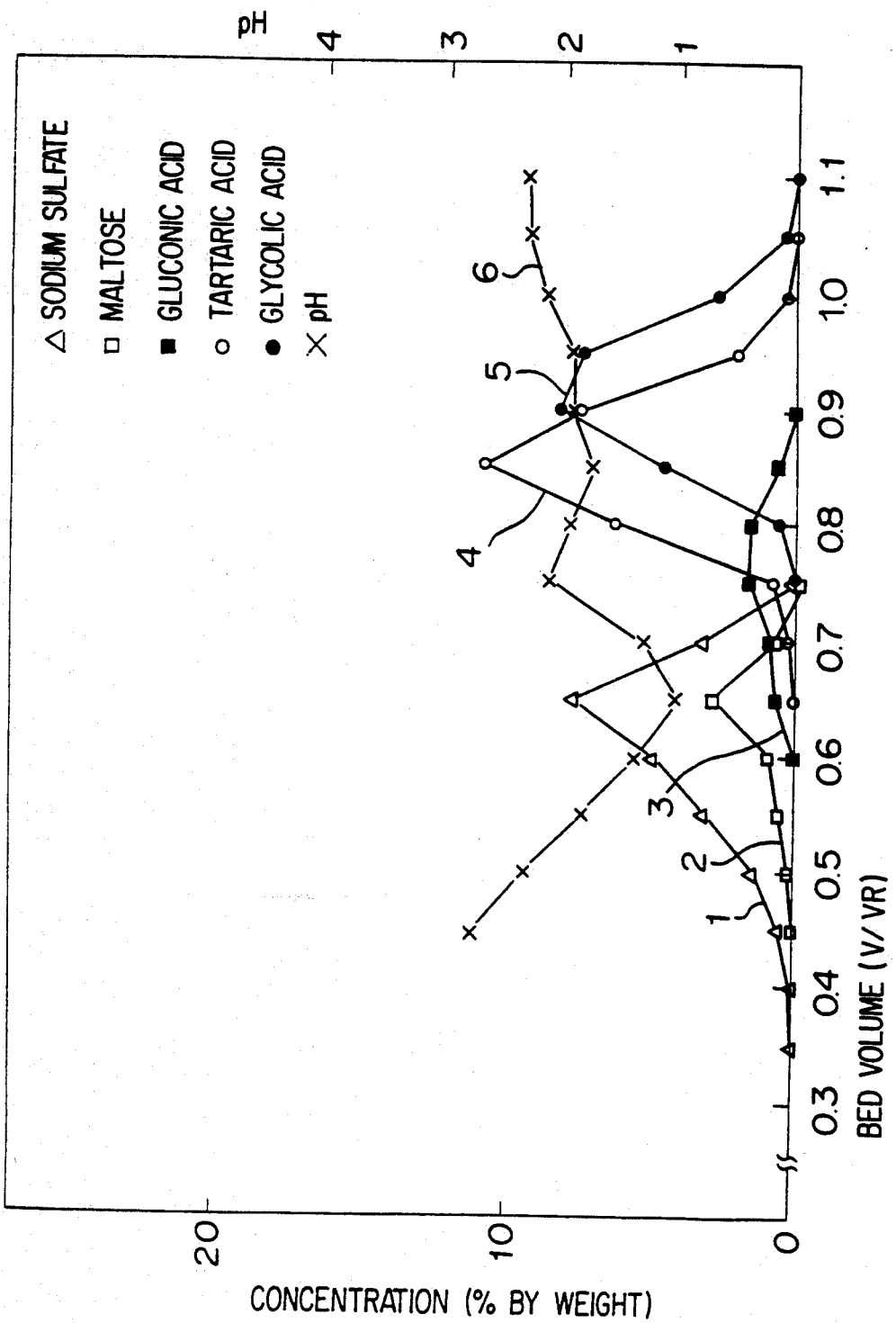
FIG. 10 is a graph showing the composition and the pH of the eluate in the first step in Example 9.

As shown in FIG. 10, the pH of the eluate was from 2.85 to 1.05 and was maintained to be always lower than the primary ionization constant (pKa: 2.98) of tartaric acid. A fraction with a bed volume (V/VR) of from 0.75 to 1.05 was separated as a tartaric acid fraction.

Figure 11:
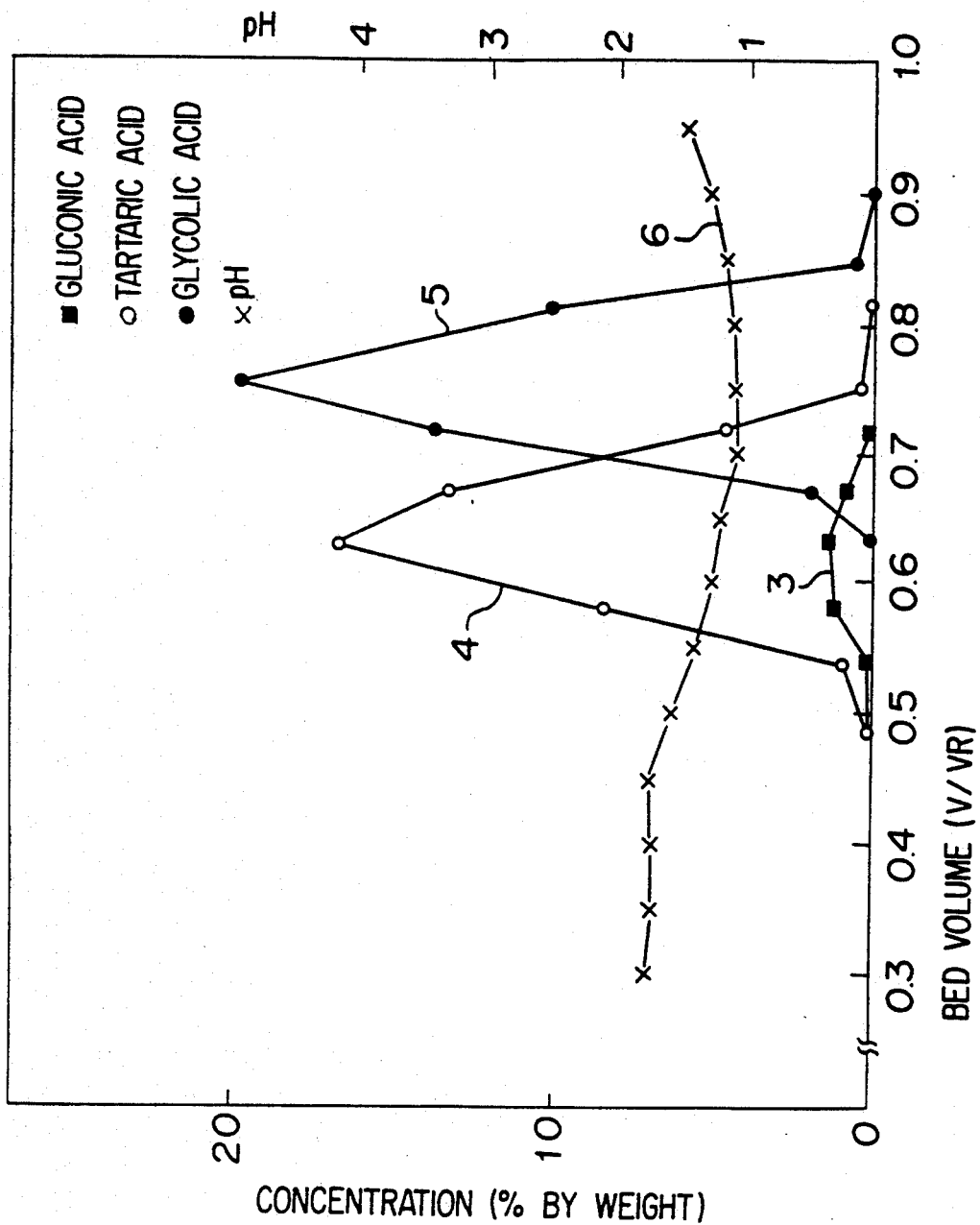
FIG. 11 is a graph showing the composition and the pH of the eluate in the second step in Example 9.

Then, this tartaric acid fraction was contacted with a H type resin of a strongly acidic cation exchange resin Diaion SK1B to remove sodium, and then concentrated. Then, sulfuric acid was added thereto to bring the pH to 0.70. The composition of the solution was analyzed, whereby the dissolved solid content concentration was found to be 48.6%, and the contents of the respective components based on the dissolved solid component were 4.5% of gluconic acid, 50.6% of tartaric acid and 45.0% of glycolic acid. On the other hand, 167 ml of Diaion UBK530 (H type) was packed as a separating agent to a second separation column, and from the top of this column, 120 ml of a 0.1% dilute sulfuric acid aqueous solution (pH: 1.7) was permitted to flow through. Then, 15 ml of the above tartaric acid fraction obtained from the first separation column was permitted to flow from the top of the second column at a flow rate of 65 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 11.

Further, a fraction with a bed volume of from 0.5 to 0.7 (V/VR) of the eluate was obtained as a tartaric acid fraction. The pH of the tartaric acid fraction was from 1.1 to 1.6. After the tartaric acid fraction, a fraction with a bed volume up to 0.9 (V/VR) was taken as a glycolic acid fraction, and the pH of this fraction was from 1.1 to 1.5. The purity of tartaric acid based on the dissolved solid content in the tartaric acid fraction obtained in the first or the second separation column was 50.6% or 83.9%, respectively.

EXAMPLE 10

In the same manner as in Example 2, a makeup solution was prepared as follows.

A mixture comprising 1.9% of sodium chloride, 1.5% of maltose, 7.5% of gluconic acid (pKa: 3.60), 47.5% of tartaric acid (pKa: 2.98) and 41.6% of glycolic acid (pKa: 3.83), was dissolved in water to obtain an aqueous solution having a concentration of 46.7%, and then concentrated sulfuric acid was added thereto to obtain an organic acid-containing solution having pH 0.71.

On the other hand, 150 ml of Diaion UBK530 (Na type) was packed in the same separation column as used in Example 1, and from the top of the column, 150 ml of a 0.1% dilute sulfuric acid aqueous solution (pH: 1.7) was permitted to flow so that the pH of the eluate from the bottom became lower than the pKa (2.98) of tartaric acid, which is the smallest among the pKa of the above three types of organic acids.

Then, 15 ml of the above organic acid-containing solution was permitted to flow from the top of the column at a flow rate of 84 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 12.

Figure 12:
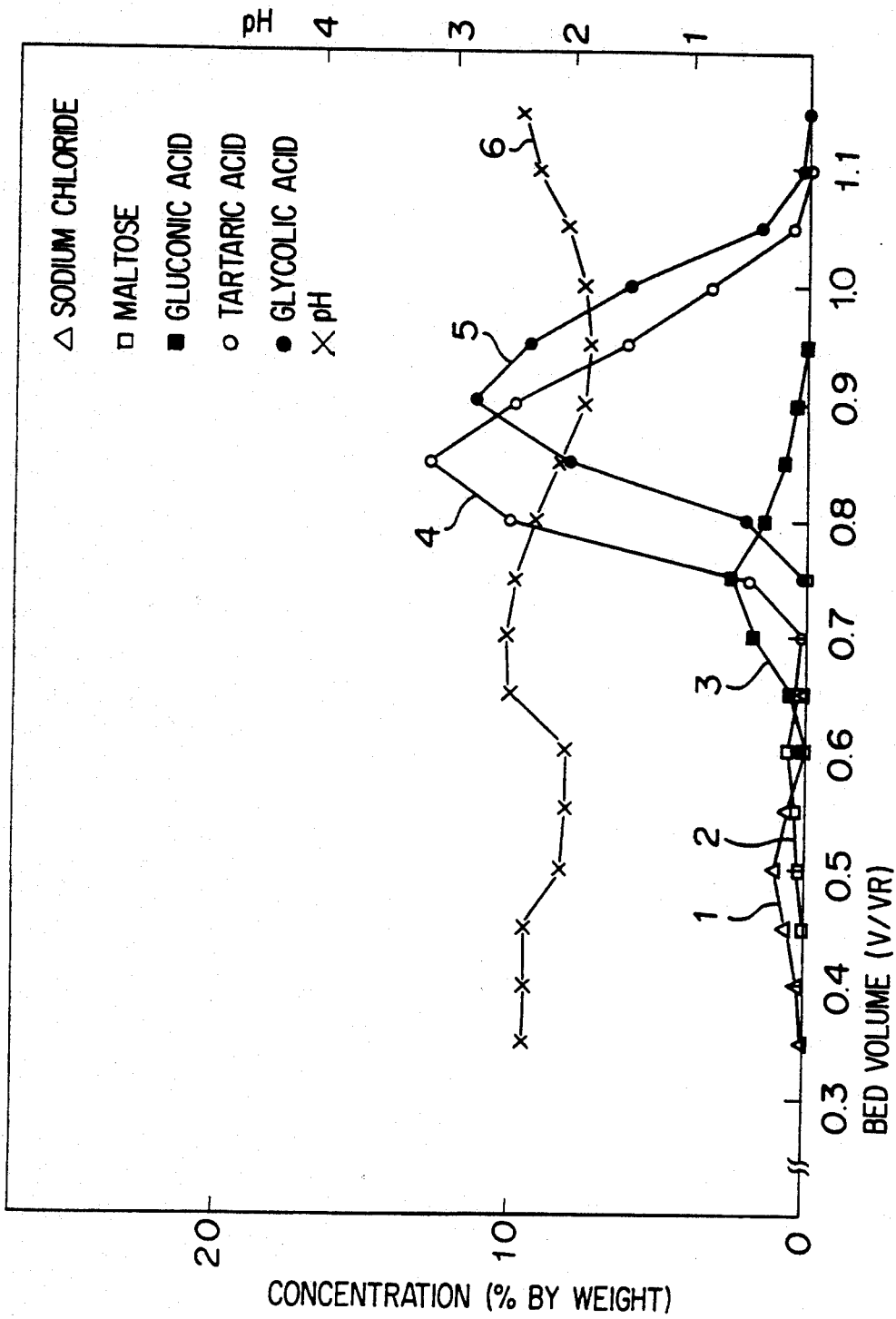
FIG. 12 is a graph showing the composition and the pH of the eluate in Example 10.

As shown in FIG. 12, the pH of the eluate was from 1.85 to 2.55 and was maintained to be always lower than the primary ionization constant (pKa: 2.98) of tartaric acid. A fraction with a bed volume (V/VR) of from 0.75 to 1.15 was separated as a tartaric acid fraction.

Then, this tartaric acid fraction was contacted with a H type resin of Diaion SK1B to remove sodium, followed by concentration. Then, sulfuric acid was added thereto to bring the pH to 0.68. The composition of this solution was analyzed, whereby the dissolved solid content concentration was found to be 48.6%, and the contents of the respective components based on the dissolved solid contents were found to be 4.3% of gluconic acid, 50.5% of tartaric acid and 45.2% of glycolic acid.

On the other hand, 120 ml of Diaion UBK530 (H type) was packed as a separating agent in a second separation column, and from the top of the column, 120 ml of a 0.1% dilute sulfuric acid aqueous solution (pH: 1.7) was permitted to flow. Then, 12 ml of the above tartaric acid fraction obtained from the first separation column was permitted to flow from the top of the second separation column at a flow rate of 71 ml/hr at a temperature of 35° C., and then a 0.1% sulfuric acid aqueous solution was permitted to flow as an eluent at the same temperature and the same flow rate, whereupon a fraction with a bed volume of from 0.5 to 0.7 (V/VR) of the eluate was collected as a tartaric acid fraction. The pH of the tartaric acid fraction was from 1.1 to 1.6. After the tartaric acid fraction, a fraction with a bed volume of up to 0.9 (V/VR) was taken as a glycolic acid fraction, and the pH of this fraction was from 1.1 to 1.5. The purity of tartaric acid based on the dissolved solid content in the tartaric acid fraction obtained from the first or the second separation column, was 50.5% or 83.6%, respectively.

EXAMPLE 11

Using the organic acid fraction containing tartaric acid and glycolic acid as the main components, obtained in Example 2, separation of tartaric acid and glycolic acid was further conducted in a second separation column. The organic acid fraction in Example 2 was contacted with a H type resin of Diaion SK1B to remove sodium, followed by concentration. Then, sulfuric acid was added thereto to bring the pH to 1.35. The composition of this solution was analyzed, whereby the dissolved solid content concentration was found to be 46.5%, and the contents of the respective components based on the dissolved solid content were found to be 4.9% of gluconic acid, 48.4% of tartaric acid and 46.7% of glycolic acid. On the other hand, 120 ml of Diaion UBK530 (Na/H type ratio: 30/70) was packed as a separating agent in a second separation column, and from the top of this column, 120 ml of a 0.1% dilute sulfuric acid aqueous solution (pH: 1.7) was permitted to flow through. Then, 12 ml of the above tartaric acid fraction obtained from the first separation column was permitted to flow from the top of the second separation column at a flow rate of 67 ml/hr at a temperature of 35° C., and then a 0.1% sulfuric acid aqueous solution was permitted to flow as an eluent at the same temperature and the same flow rate, whereupon a fraction with a bed volume of from 0.50 to 0.775 (V/VR) of the eluate was collected as a tartaric acid fraction. The pH of the tartaric acid fraction was from 1.6 to 2.0. After the tartaric acid fraction, a fraction with a bed volume of up to 1.0 (V/VR) was taken as a glycolic acid fraction, and the pH of this fraction was from 1.7 to 2.2. The purity of tartaric acid based on the dissolved solid content in the tartaric acid fraction obtained from the first or the second separation column was 48.4% or 71.6%, respectively.

EXAMPLE 12

Using the organic acid fraction containing tartaric acid and glycolic acid as the main components, obtained in Example 3, separation of tartaric acid and glycolic acid was conducted by a second separation column. The organic acid fraction in Example 3 was contacted with a H type resin of Diaion SK1B to remove sodium, followed by concentration. Then, sulfuric acid was added thereto to bring the pH to 1.68. The composition of the solution was analyzed, whereby the dissolved solid content concentration was found to be 48.0%, and the contents of the respective components based on the dissolved solid content were found to be 5.6% of gluconic acid, 44.7% of tartaric acid and 49.7% of glycolic acid. On the other hand, 120 ml of Diaion UBK530 (Na/H type ratio: 70/30) was packed as a separating agent to a second separation column, and from the top of the column, 120 ml of a 0.1% dilute sulfuric acid aqueous solution (pH: 1.7) was permitted to flow through. Then, 12 ml of the above tartaric acid fraction obtained from the first separation column was permitted to flow from the top of the second separation column at a flow rate of 61 ml/hr at a temperature of 35° C., and then a 0.1% sulfuric acid aqueous solution was permitted to flow as an eluent at the same temperature and the same flow rate, whereupon a fraction with a bed volume of from 0.55 to 0.85 (V/VR) of the eluate was collected as a tartaric acid fraction. The pH of the tartaric acid fraction was from 1.8 to 2.5. After the tartaric acid fraction, a fraction up to a bed volume of 1.05 (V/VR) was taken as a glycolic acid fraction, and the pH of this fraction was from 2.0 to 2.4. The purity of tartaric acid to the dissolved solid content in the tartaric acid fraction obtained in the first or the second separation column was 44.7% or 57.7%, respectively.

EXAMPLE 13

To the supernatant of the culture medium obtained in Example 4, glycolic acid, tartaric acid, gluconic acid and their salts, sodium sulfate and maltose were added, and sulfuric acid was further added thereto to bring the pH to 1.70. The organic acid-containing solution thereby obtained, was analyzed. As a result, its composition was found to be 23.1% of sodium sulfate, 7.7% of maltose, 4.1% of gluconic acid (pKa: 3.60), 34.7% of tartaric acid (pKa: 2.98) and 30.4% of glycolic acid (pKa: 3.83), and the concentration was 47.5%.

On the other hand, 130 ml of Diaion UBK530 (Mg type) was packed in the same separation column as used in Example 1, and from the top of the column, 130 ml of a 0.1% dilute sulfuric acid aqueous solution (pH: 1.7) was permitted to flow so that the pH of the eluate from the bottom became lower than the pKa (2.98) of tartaric acid, which is the smallest among the pKa of the above three types of organic acids.

Then, 13 ml of the above organic acid-containing solution was permitted to flow from the top of the column at a flow rate of 65 ml/hr at a temperature of 35° C., and then a 0.1% sulfuric acid aqueous solution was permitted to flow as an eluent at the same temperature and the same flow rate, whereby the composition and the pH of the eluate from the bottom of the column were measured. The results are shown in FIG. 13.

Figure 13:
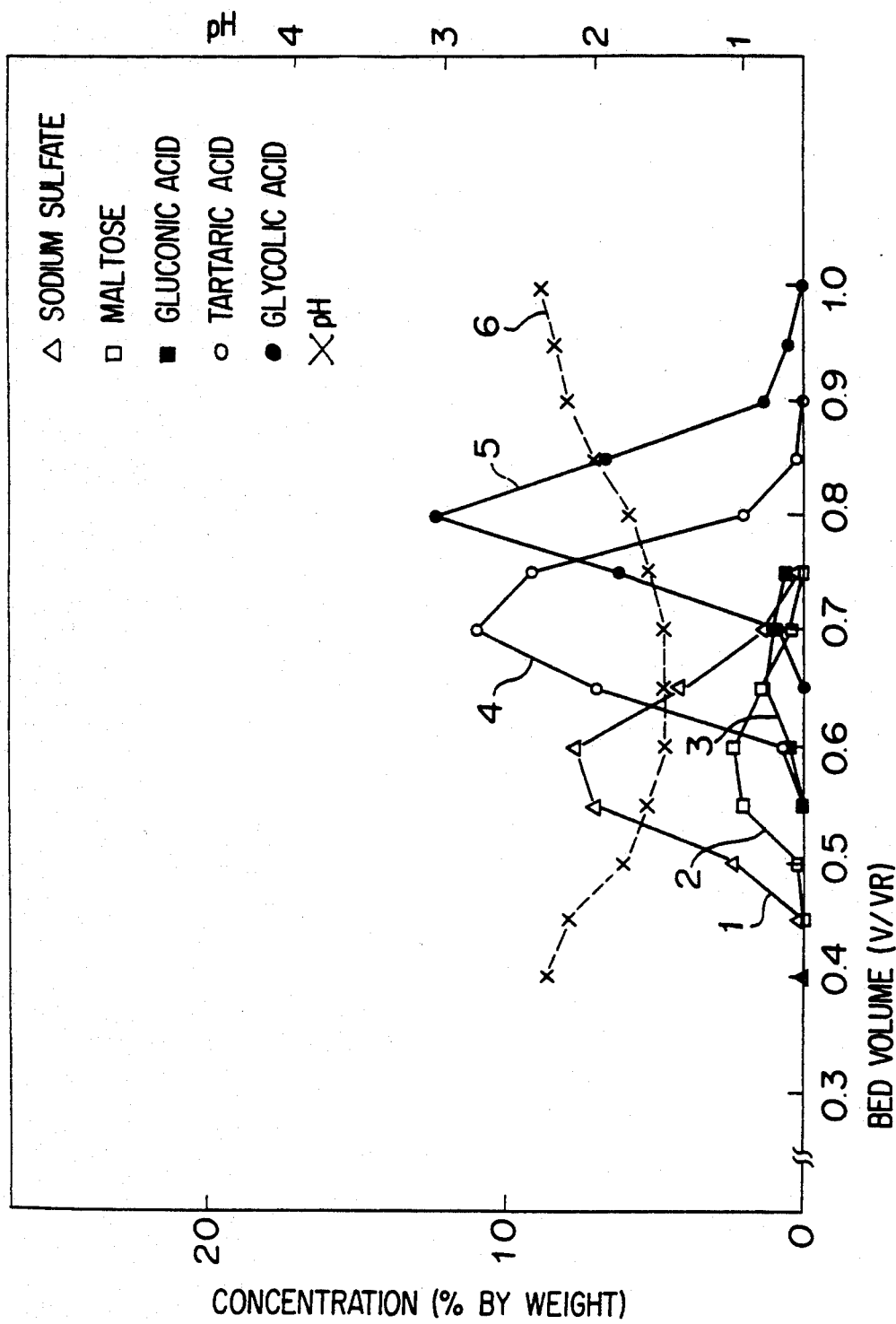
FIG. 13 is a graph showing the composition and the pH of the eluate in Example 13.

As shown in FIG. 13, the pH of the eluate was from 1.56 to 2.36 and was maintained to be always lower than the primary ionization constant (pKa: 2.98) of tartaric acid. As compared with Example 11 employing the Na type separating agent, the organic acid started to elute quickly. Therefore, separation between the salts and the organic acids are not complete. However, it is possible to separate a fraction containing mainly inorganic salts and a fraction containing mainly organic acids. A fraction with a bed volume (V/VR) of from 0.675 to 1.0 was separated as a tartaric acid fraction.

Then, this tartaric acid fraction was contacted with a H type resin of Diaion SKIB to remove sodium, followed by concentration. Then, sulfuric acid was added thereto to bring the pH to 0.69. The composition of this solution was analyzed, whereby the dissolved solid content concentration was found to be 48.4%, and the contents of the respective components based on the dissolved solid content were found to be 1.1% of maltose, 3.0% of gluconic acid, 43.6% of tartaric acid and 52.3% of glycolic acid. On the other hand, 120 ml of Diaion UBK530 (H type) was packed as a separating agent in a second separation column, and from the top of this column, 120 ml of a 0.1% dilute sulfuric acid aqueous solution (pH: 1.7) was permitted to flow through. Then, 12 ml of the above tartaric acid fraction obtained from the first separation column was permitted to flow from the top of the second separation column at a flow rate of 71 ml/hr at a temperature of 35° C., and then a 0.1% sulfuric acid aqueous solution was permitted to flow as an eluent at the same temperature and the same flow rate, whereupon a fraction with a bed volume of from 0.5 to 0.7 (V/VR) of the eluate was collected as a tartaric acid fraction. The pH of the tartaric acid fraction was from 1.0 to 1.5. After the tartaric acid fraction, a fraction with a bed volume of up to 0.9 (V/VR) was taken as a glycolic acid fraction, and the pH of this fraction was from 1.0 to 1.6. The purity of tartaric acid based on the dissolved solid content in the tartaric acid fraction obtained in the first or the second separation column was 43.6% or 80.7%, respectively.

EXAMPLE 14

Using the organic acid fraction containing tartaric acid and glycolic acid as the main components, obtained in Example 7, separation of tartaric acid and glycolic acid was conducted by a second separation column. The organic acid fraction in Example 7 was contacted with a H type resin of Diaion SKIB to remove sodium, followed by concentration. Then, sulfuric acid was added thereto to bring the pH to 0.70. The composition of this solution was analyzed, whereby the dissolved solid content concentration was found to be 48.1%, and the contents of the respective components based on the dissolved solid content were found to be 3.9% of gluconic acid, 53.1% of tartaric acid and 43.0% of glycolic acid. On the other hand, 60 ml of Diaion UBK530 (H type) was packed as a separating agent in a second separation column, and from the top of this column, 60 ml of a 0.1% dilute sulfuric acid aqueous solution (pH: 1.7) was permitted to flow through. Then, 6 ml of the above tartaric acid fraction obtained from the first separation column was permitted to flow from the top of the second separation column at a flow rate of 36 ml/hr at a temperature of 35° C., and then a 0.1% sulfuric acid aqueous solution was permitted to flow as an eluent at the same temperature and the same flow rate, whereupon a fraction with a bed volume of from 0.5 to 0.7 (V/VR) of the eluate was collected as a tartaric acid fraction. The pH of the tartaric acid fraction was from 1.0 to 1.6. After the tartaric acid fraction, a fraction with a bed volume of up to 0.9 (V/VR) was taken as a glycolic acid fraction, and the pH of this fraction was from 1.0 to 1.6. The purity of tartaric acid based on the dissolved solid content in the tartaric acid fraction obtained in the first or the second separation column was 53.1% or 85.2%, respectively.

REFERENCE EXAMPLE 1

In the same manner as in Example 2, a makeup solution was prepared as follows.

A mixture comprising 1.9% of sodium chloride, 1.8% of glucose, 5.8% of gluconic acid (pKa: 3.60), 45.5% of tartaric acid (pKa: 2.98) and 45.0% of glycolic acid (pKa: 3.83), was dissolved in water to obtain an aqueous solution having a concentration of 50.3%. Then, concentrated sulfuric acid was added thereto to obtain an organic acid-containing solution having pH 0.69.

On the other hand, 167 ml of Diaion UBK530 (Na type) was packed in the same separation column as used in Example 1, and washed sufficiently with water.

Figure 14:
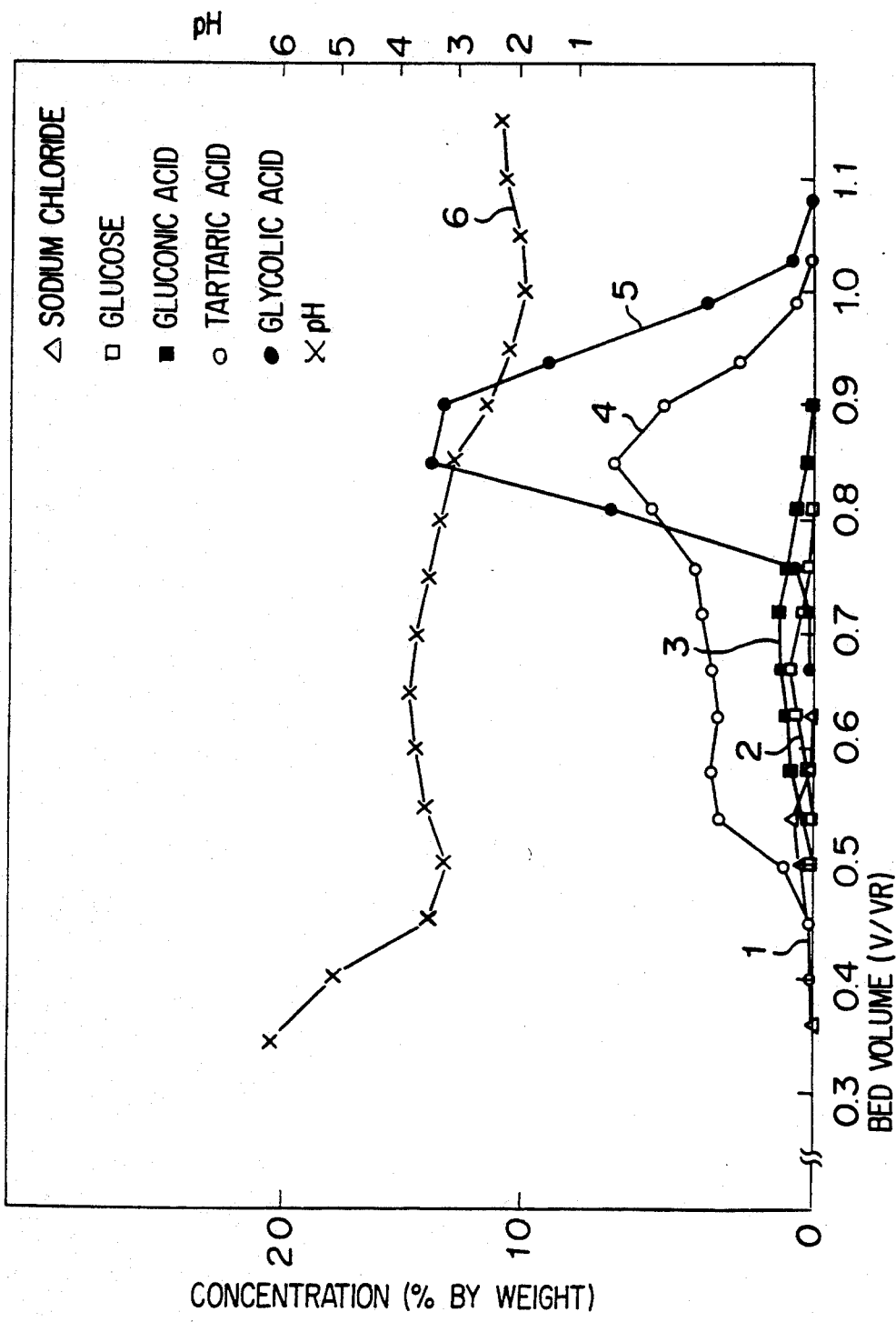
FIG. 14 is a graph showing the composition and the pH of the eluate in the first step in Reference Example 1.

Then, 17 ml of the above organic acid-containing solution was permitted to flow from the top of the column at a flow rate of 84 ml/hr at a temperature of 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 14.

The above organic acid-containing solution was permitted to flow without preliminarily washing the separation column packed with the separation agent with 0.1% sulfuric acid to bring the pH of the solution in the separation column to a level of lower than the pKa 2.98 of tartaric acid. Therefore, the pH of the solution in the column increased. As a result, part of tartaric acid was converted to a tartaric acid salt, which started to elute at the same bed volume of 0.40 as sodium chloride. On the other hand, gluconic acid or glycolic acid having pKa higher than tartaric acid was not substantially affected since the proportion to be converted to the organic acid salts was less, although the bed volume at which elution started from the separation column was more or less quickened. The pH of the eluate was initially 6.7, but dropped to 2.3 at the end of the elution.

Then, using the same separation column as used in Reference Example 1 as it is, the solution treated in Reference Example 1 was permitted to flow again in an amount of 17 ml at a flow rate of 84 ml/hr at 35° C., and then a 0.1% sulfuric acid aqueous solution was permitted to flow as an eluent at the same temperature and the same flow rate, whereupon the composition and the pH of the eluate from the bottom of the column were measured. The results are shown in FIG. 15.

Figure 15:
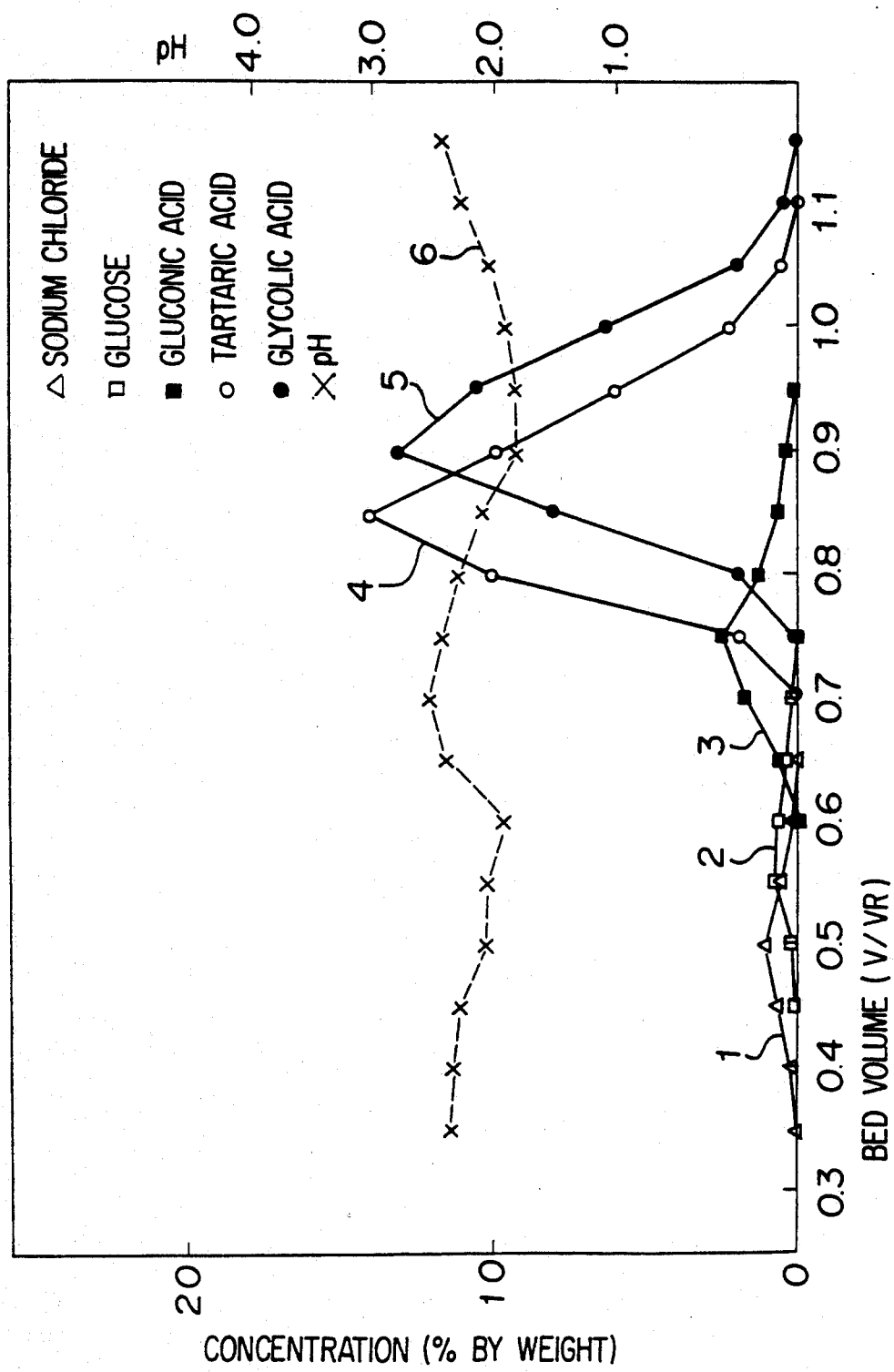
FIG. 15 is a graph showing the composition and the pH of the eluate in the second step in Reference Example 1.

As shown in FIG. 15, the pH of the eluate was from 1.90 to 2.50 and was maintained to be always lower than the primary ionization constant (pKa: 2.98) of tartaric acid. Further, by separating the eluate into two fractions i.e. the preceding fraction and the later fraction with the separating point being at a bed volume (V/VR) of 0.75, it was possible to separate and recover a fraction having a high content of tartaric acid.

According to the process of the present invention, when the organic acid-containing solution is contacted with a cation exchange resin to adsorb organic acids on the resin, followed by desorbing the organic acids with an eluent to separate the organic acids from the organic acid-containing solution, the adsorbing treatment is conducted under such a condition that the pH of the organic acid-containing solution is maintained at a level lower than the pKa of the organic acid, whereby the organic acid can efficiently be separated from other components. Thus, the contribution of the present invention to the industrial production of organic acids is significant.

We claim:

1. A process for separating an organic acid or acids from an organic-acid-containing solution obtained by a fermentation method in which glucose is used as starting material, which process comprises contacting said organic acid-containing solution with a cation exchange resin to adsorb the organic acid or acids on the cation exchange resin, then contacting the cation exchange resin with an eluent to desorb the organic acid or acids, and then separating from the eluate a solution containing the organic acid or acids, wherein said organic acid-containing solution is contacted with the cation exchange resin under such a condition that the pH of the organic acid-containing solution is maintained at a pH level lower than pKa, where Ka is the ionization constant of the organic acid or acids or the primary ionization constant in a case of a polybasic acid or acids, and the pH of the eluate is maintained at the above pH level.

2. The process according to claim 1, wherein the organic acid-containing solution contains tartaric acid.

3. The process according to claim 1, wherein the organic acid-containing solution contains one or more acids selected from the group consisting of citric acid, lactic acid, gluconic acid and glycolic acid.

4. The process according to claim 1, wherein the organic acid-containing solution contains tartaric acid and one or more acids selected from the group consisting of citric acid, lactic acid, gluconic acid and glycolic acid.

5. The process according to any one of claims 1 to 4, wherein the cation exchange resin is a strongly acidic cation exchange resin of a divinylbenzene cross-linked polystyrene sulfonic acid type.

6. The process according to claim 4, wherein an organic acid fraction is separated by means of a first separation column packed with a resin which is a strongly acidic cation exchange resin of a divinylbenzene cross-linked polystyrene sulfonic acid type wherein the proportion of the counter ion of sulfonic acid being hydrogen is at most 70%, and then said organic acid fraction is further subjected to separation by means of a second separation column packed with a resin which is a strongly acidic cation exchange resin of a divinylbenzene cross-linked polystyrene sulfonic acid type in which the proportion of the counter ion of sulfonic acid being hydrogen is at least 30%, to separate tartaric acid.

7. The process according to any one of claims 1 to 6, wherein the eluent is an inorganic acid solution.

8. The process according to claim 7, wherein the inorganic acid solution is a dilute aqueous sulfuric acid solution having a concentration of not higher than 1 equivalent/l.

* * * * *